US008697665B2

(12) United States Patent
Fontanellas Romá et al.

(10) Patent No.: US 8,697,665 B2
(45) Date of Patent: Apr. 15, 2014

(54) PORPHOBILINOGEN DEAMINASE GENE THERAPY

(75) Inventors: Antonio Fontanellas Romá, Pamplona Navarra (ES); Gloria González Aseguinolaza, Pamplona Navarra (ES); Maria Sol Rodriguez Pena, Le Mont-sur-Lausanne (CH); Maria Astrid Pañeda Rodriguez, Pamplona Navarra (ES); Jaap Twisk, Amsterdam (NL); Jesús Maria Prieto Valtueña, Pamplona Navarra (ES); Harald Petry, Amsterdam (NL); Sander Jan Hendrik Van Deventer, Amsterdam (NL)

(73) Assignees: Proyecto de Biomedicina CIMA S.L., Pamplona Navarra (ES); Uniqure Biopharma B.V., Amsterdam (NL)

( * ) Notice: Subject to any disclaimer, the term of this patent is extended or adjusted under 35 U.S.C. 154(b) by 0 days.

(21) Appl. No.: 13/121,532

(22) PCT Filed: Sep. 29, 2009

(86) PCT No.: PCT/NL2009/050584
§ 371 (c)(1),
(2), (4) Date: Jul. 14, 2011

(87) PCT Pub. No.: WO2010/036118
PCT Pub. Date: Apr. 1, 2010

(65) Prior Publication Data
US 2011/0262399 A1    Oct. 27, 2011

Related U.S. Application Data

(60) Provisional application No. 61/100,881, filed on Sep. 29, 2008.

(30) Foreign Application Priority Data

Sep. 29, 2008 (EP) .................................. 08165393

(51) Int. Cl.
*A61K 48/00* (2006.01)
*C12N 15/00* (2006.01)

(52) U.S. Cl.
USPC .................. 514/44 R; 424/93.2; 435/320.1

(58) Field of Classification Search
USPC ................... 514/44 R; 424/93.21; 435/320.1
See application file for complete search history.

(56) References Cited

U.S. PATENT DOCUMENTS

2009/0175860 A1 * 7/2009 Stover et al. ............... 424/133.1

FOREIGN PATENT DOCUMENTS

| EP | 1 049 487 B | | 5/2002 |
| WO | 9937325 | | 7/1999 |
| WO | WO/2007/046703 | * | 4/2007 |
| WO | WO2007047520 | * | 4/2007 |
| WO | WO 2007047520 A | | 4/2007 |

OTHER PUBLICATIONS

Johansson et al (Mol Ther, 2004, 10: 337-343.*
Kaiser Science, 317, 2007, 580.*
Ecke, Goodman & Gilman's The Pharmacological basis of Therapeutics, 1996, McGraw-Hill, New York, NY. pp. 77-101.*
Walsh Gene Therapy, 2003, 10, 999-1003.*
Paneda et al , Human Gene Ther., 2009, 20(8), 908-917.*
Amsterdam Molecular Press release(May 1, 2007, IDS).*
Yasuda et al The Journal of Gene Medicine, 2007, 806-811.*
NCBi accession No. X04808, dated Apr. 18, 2005.*
Gustafsson et al (Trends in Biotechnology, 2004, 22, 346-353.*
Gautama et al (Am J Respir Med, 2002;1(1):35-46.*
Xiao (Mol Ther. 2000; 1(4):323-9.*
Ponder et al (Current Opinion Hematol, 2006, 13, 301-307.*
Sobrevals et al Gene therapy, 2012, 19, 411-417.*
Kramer et al., 2003, Mol Ther. 7(3):375-85, abstract.*
Johansson, et al., "Correction of the biochemical defect in porphobilinogen deaminase deficient cells by non-viral gene delivery", Molecular and Cellular Biochemistry 250:65-71, 2003.
Yasuda, et al., "Acute intermittent porphyria: vector optimization for gene therapy", J Gene Med9:806-811, 2007t.
Amsterdam Molecular Therapeutics press release, http://www.drugs.com/clinical_trials/amsterdam-molecular-therapeutics-bv-present-preclinical-proof-concept-data-gene-therapy-amt-020-747.html?printable=1, May 1, 2007.
Haas, et al., "Codon Usage Limitation in Expression of HIV-1 Envelope Glycoprotein", Curr Biology, 6:315-324, 1996.
Gustafsson, et al., "Codon bias and heterologous protein expression", Trends in Biotechnology,22:346-353, 2004.
Johansson, et al., "Adenoviral-mediated expression of porphobilinogen deaminase in liver restores the metabolic defect in a mouse model of acute intermittent porphyria", Molecular Therapy, 10:337-343, 2004.

(Continued)

*Primary Examiner* — Anoop Singh
(74) *Attorney, Agent, or Firm* — Browdy and Neimark, PLLC

(57) ABSTRACT

The present invention relates to nucleotide sequences coding for human porphobilinogen deaminase that are optimised for higher expression in mammalian cells. The invention further relates to DNA constructs comprising such optimised synthetic coding sequences for use in gene therapy of conditions caused by a deficiency in porphobilinogen deaminase, such as acute intermittent porphyria. Accordingly, the present invention relates to a nucleic acid or a nucleic acid construct comprising a nucleotide sequence coding for a human porphobilinogen deaminase, wherein at least 320 of the codons coding for the human porphobilinogen deaminase are identical to the codons in SEQ ID NO: 1 or wherein at least 305 of the codons coding for the human porphobilinogen deaminase are identical to the codons in SEQ ID NO: 3.

5 Claims, 8 Drawing Sheets

(56) References Cited

OTHER PUBLICATIONS

Chretien, et al., "Alternative Transcription and Splicing of the Human Porphobilinogen Deaminase Gene Result Either in Tissue-Specific or in Housekeeping Expression", Proc Nat'l Acad Sci USA 85:6-10, 1988.

Grandchamp, "Acute intermittent porphyria", Sem Liver Dis, 18:17-24, 1998.

Unzo et al., "Sustained Enzymatic Correction by rAAV-Mediated Liver Gene Therapy Protects Against Induced Motor Neuropathy in Acute Porphyria Mice", Molecular Therapy, 19 (2):243-250 Feb. 2011.

Mittal et al., "Metabolic Analysis in Transgenic Mouse Models of Acute Intermittent Porphyria (AIP)" 1 page, Abstract from International Congress of Porphyrins and Porphyrias, May 2013.

de Verneuil et al, "Porphyrias: Animal Models and Prospects for Cellular and Gene Therapy" Journal of Bioenergetics and Biomembranes, 27:239-248, Feb. 1995.

Clavero et al., "Feline acute intermittent porphyria: a phenocopy masquerading as an erythropoietic porphyria due to dominant and recessive hydroxymethylbilane synthase mutations" Human Molecular Genetics, 19::584-596, Nov. 24, 2009.

\* cited by examiner

SEQUENCE LISTING

<160> NUMBER OF SEQ ID NOS: 10

<210> SEQ ID NO 1
<211> LENGTH: 1089
<212> TYPE: DNA
<213> ORGANISM: Artificial
<220> FEATURE:
<223> OTHER INFORMATION: optimised coding sequence
<220> FEATURE:
<221> NAME/KEY: CDS
<222> LOCATION: (1)..(1083)

<400> SEQUENCE: 1

| | | | | | | | | | | | | | | | | |
|---|---|---|---|---|---|---|---|---|---|---|---|---|---|---|---|---|
| atg | agc | ggc | aac | ggc | aac | gcc | gca | gcc | acc | gcc | gag | gaa | aac | agc | ccc | 48 |
| Met | Ser | Gly | Asn | Gly | Asn | Ala | Ala | Ala | Thr | Ala | Glu | Glu | Asn | Ser | Pro | |
| 1 | | | | 5 | | | | | 10 | | | | | 15 | | |
| aag | atg | cgg | gtg | atc | aga | gtg | ggc | acc | cgg | aag | agc | cag | ctg | gcc | cgg | 96 |
| Lys | Met | Arg | Val | Ile | Arg | Val | Gly | Thr | Arg | Lys | Ser | Gln | Leu | Ala | Arg | |
| | | | 20 | | | | | 25 | | | | | 30 | | | |
| atc | cag | acc | gac | agc | gtg | gtg | gcc | acc | ctg | aag | gcc | tcc | tac | ccc | ggc | 144 |
| Ile | Gln | Thr | Asp | Ser | Val | Val | Ala | Thr | Leu | Lys | Ala | Ser | Tyr | Pro | Gly | |
| | | | | 35 | | | | | 40 | | | | | 45 | | |
| ctg | cag | ttc | gag | atc | att | gcc | atg | agc | acc | acc | ggc | gac | aag | atc | ctg | 192 |
| Leu | Gln | Phe | Glu | Ile | Ile | Ala | Met | Ser | Thr | Thr | Gly | Asp | Lys | Ile | Leu | |
| | | 50 | | | | | 55 | | | | | 60 | | | | |
| gac | acc | gcc | ctg | agc | aag | atc | ggc | gag | aag | agc | ctg | ttc | aca | aaa | gag | 240 |
| Asp | Thr | Ala | Leu | Ser | Lys | Ile | Gly | Glu | Lys | Ser | Leu | Phe | Thr | Lys | Glu | |
| 65 | | | | | 70 | | | | | 75 | | | | | 80 | |
| ctg | gaa | cac | gcc | ctg | gaa | aag | aac | gag | gtg | gac | ctg | gtg | gtg | cac | agc | 288 |
| Leu | Glu | His | Ala | Leu | Glu | Lys | Asn | Glu | Val | Asp | Leu | Val | Val | His | Ser | |
| | | | | 85 | | | | | 90 | | | | | 95 | | |
| ctg | aag | gac | ctg | ccc | acc | gtg | ctg | ccc | cct | ggc | ttc | acc | atc | ggc | gcc | 336 |
| Leu | Lys | Asp | Leu | Pro | Thr | Val | Leu | Pro | Pro | Gly | Phe | Thr | Ile | Gly | Ala | |
| | | | 100 | | | | | 105 | | | | | 110 | | | |
| atc | tgc | aag | aga | gag | aac | ccc | cac | gac | gcc | gtg | gtg | ttc | cac | cct | aag | 384 |
| Ile | Cys | Lys | Arg | Glu | Asn | Pro | His | Asp | Ala | Val | Val | Phe | His | Pro | Lys | |
| | | | 115 | | | | | 120 | | | | | 125 | | | |
| ttc | gtg | ggc | aag | aca | ctg | gaa | acc | ctg | ccc | gag | aag | tcc | gtg | gtg | ggc | 432 |
| Phe | Val | Gly | Lys | Thr | Leu | Glu | Thr | Leu | Pro | Glu | Lys | Ser | Val | Val | Gly | |
| | | 130 | | | | | 135 | | | | | 140 | | | | |
| acc | agc | agc | ctg | cgg | aga | gcc | gcc | cag | ctg | cag | cgg | aag | ttc | ccc | cac | 480 |
| Thr | Ser | Ser | Leu | Arg | Arg | Ala | Ala | Gln | Leu | Gln | Arg | Lys | Phe | Pro | His | |
| 145 | | | | | 150 | | | | | 155 | | | | | 160 | |
| ctg | gaa | ttt | cgg | agc | atc | cgg | ggc | aac | ctg | aac | acc | cgg | ctg | cgg | aag | 528 |
| Leu | Glu | Phe | Arg | Ser | Ile | Arg | Gly | Asn | Leu | Asn | Thr | Arg | Leu | Arg | Lys | |
| | | | | 165 | | | | | 170 | | | | | 175 | | |
| ctg | gac | gag | cag | cag | gaa | ttt | tcc | gct | atc | atc | ctg | gcc | aca | gcc | gga | 576 |
| Leu | Asp | Glu | Gln | Gln | Glu | Phe | Ser | Ala | Ile | Ile | Leu | Ala | Thr | Ala | Gly | |
| | | | 180 | | | | | 185 | | | | | 190 | | | |
| ctg | cag | cgg | atg | ggc | tgg | cac | aac | aga | gtg | ggc | cag | atc | ctg | cac | ccc | 624 |
| Leu | Gln | Arg | Met | Gly | Trp | His | Asn | Arg | Val | Gly | Gln | Ile | Leu | His | Pro | |
| | | | 195 | | | | | 200 | | | | | 205 | | | |
| gag | gaa | tgc | atg | tac | gcc | gtg | ggc | cag | gga | gcc | ctg | ggc | gtg | gaa | gtg | 672 |
| Glu | Glu | Cys | Met | Tyr | Ala | Val | Gly | Gln | Gly | Ala | Leu | Gly | Val | Glu | Val | |
| | | 210 | | | | | 215 | | | | | 220 | | | | |
| cgg | gcc | aag | gac | cag | gac | atc | ctg | gat | ctg | gtg | ggc | gtg | ctg | cat | gac | 720 |
| Arg | Ala | Lys | Asp | Gln | Asp | Ile | Leu | Asp | Leu | Val | Gly | Val | Leu | His | Asp | |
| 225 | | | | | 230 | | | | | 235 | | | | | 240 | |
| ccc | gag | aca | ctg | ctg | cgg | tgt | atc | gcc | gag | cgg | gcc | ttc | ctg | cgg | cac | 768 |
| Pro | Glu | Thr | Leu | Leu | Arg | Cys | Ile | Ala | Glu | Arg | Ala | Phe | Leu | Arg | His | |
| | | | | 245 | | | | | 250 | | | | | 255 | | |

```
ctg gaa ggc ggc tgc agc gtg ccc gtg gcc gtg cac acc gcc atg aag    816
Leu Glu Gly Gly Cys Ser Val Pro Val Ala Val His Thr Ala Met Lys
        260                 265                 270 gac gga cag ctg tac ctg aca ggc ggc gtg tgg agc ctg gac ggc agc    864
Asp Gly Gln Leu Tyr Leu Thr Gly Gly Val Trp Ser Leu Asp Gly Ser
    275                 280                 285 gac agc atc cag gag acc atg cag gcc acc atc cac gtg ccc gcc cag    912
Asp Ser Ile Gln Glu Thr Met Gln Ala Thr Ile His Val Pro Ala Gln
290                 295                 300 cac gag gac ggc ccc gag gac gac cct cag ctg gtc ggc atc acc gcc    960
His Glu Asp Gly Pro Glu Asp Asp Pro Gln Leu Val Gly Ile Thr Ala
305                 310                 315                 320 cgg aac atc ccc aga ggc ccc cag ctg gcc gcc cag aac ctg ggc atc   1008
Arg Asn Ile Pro Arg Gly Pro Gln Leu Ala Ala Gln Asn Leu Gly Ile
            325                 330                 335 agc ctg gcc aac ctg ctg ctg tcc aag ggc gcc aag aac atc ctg gac   1056
Ser Leu Ala Asn Leu Leu Leu Ser Lys Gly Ala Lys Asn Ile Leu Asp
        340                 345                 350 gtg gcc cgg cag ctg aac gac gcc cac tgatga                        1089
Val Ala Arg Gln Leu Asn Asp Ala His
            355                 360

<210> SEQ ID NO 2
<211> LENGTH: 361
<212> TYPE: PRT
<213> ORGANISM: Artificial
<220> FEATURE:
<223> OTHER INFORMATION: Synthetic Construct

<400> SEQUENCE: 2

Met Ser Gly Asn Gly Asn Ala Ala Ala Thr Ala Glu Glu Asn Ser Pro
1               5                   10                  15

Lys Met Arg Val Ile Arg Val Gly Thr Arg Lys Ser Gln Leu Ala Arg
            20                  25                  30

Ile Gln Thr Asp Ser Val Val Ala Thr Leu Lys Ala Ser Tyr Pro Gly
        35                  40                  45

Leu Gln Phe Glu Ile Ile Ala Met Ser Thr Thr Gly Asp Lys Ile Leu
    50                  55                  60

Asp Thr Ala Leu Ser Lys Ile Gly Glu Lys Ser Leu Phe Thr Lys Glu
65                  70                  75                  80

Leu Glu His Ala Leu Glu Lys Asn Glu Val Asp Leu Val Val His Ser
                85                  90                  95

Leu Lys Asp Leu Pro Thr Val Leu Pro Pro Gly Phe Thr Ile Gly Ala
            100                 105                 110

Ile Cys Lys Arg Glu Asn Pro His Asp Ala Val Val Phe His Pro Lys
        115                 120                 125

Phe Val Gly Lys Thr Leu Glu Thr Leu Pro Glu Lys Ser Val Val Gly
    130                 135                 140

Thr Ser Ser Leu Arg Arg Ala Ala Gln Leu Gln Arg Lys Phe Pro His
145                 150                 155                 160

Leu Glu Phe Arg Ser Ile Arg Gly Asn Leu Asn Thr Arg Leu Arg Lys
                165                 170                 175

Leu Asp Glu Gln Gln Glu Phe Ser Ala Ile Ile Leu Ala Thr Ala Gly
            180                 185                 190

Leu Gln Arg Met Gly Trp His Asn Arg Val Gly Gln Ile Leu His Pro
        195                 200                 205

Glu Glu Cys Met Tyr Ala Val Gly Gln Gly Ala Leu Gly Val Glu Val
    210                 215                 220
```

```
Arg Ala Lys Asp Gln Asp Ile Leu Asp Leu Val Gly Val Leu His Asp
225                 230                 235                 240

Pro Glu Thr Leu Leu Arg Cys Ile Ala Glu Arg Ala Phe Leu Arg His
            245                 250                 255

Leu Glu Gly Gly Cys Ser Val Pro Val Ala Val His Thr Ala Met Lys
        260                 265                 270

Asp Gly Gln Leu Tyr Leu Thr Gly Gly Val Trp Ser Leu Asp Gly Ser
    275                 280                 285

Asp Ser Ile Gln Glu Thr Met Gln Ala Thr Ile His Val Pro Ala Gln
    290                 295                 300

His Glu Asp Gly Pro Glu Asp Pro Gln Leu Val Gly Ile Thr Ala
305                 310                 315                 320

Arg Asn Ile Pro Arg Gly Pro Gln Leu Ala Ala Gln Asn Leu Gly Ile
            325                 330                 335

Ser Leu Ala Asn Leu Leu Ser Lys Gly Ala Lys Asn Ile Leu Asp
        340                 345                 350

Val Ala Arg Gln Leu Asn Asp Ala His
        355                 360
```

<210> SEQ ID NO 3
<211> LENGTH: 1038
<212> TYPE: DNA
<213> ORGANISM: Artificial
<220> FEATURE:
<223> OTHER INFORMATION: optimised coding sequence
<220> FEATURE:
<221> NAME/KEY: CDS
<222> LOCATION: (1)..(1032)

<400> SEQUENCE: 3

```
atg cgg gtg atc aga gtg ggc acc cgg aag agc cag ctg gcc cgg atc      48
Met Arg Val Ile Arg Val Gly Thr Arg Lys Ser Gln Leu Ala Arg Ile
1               5                   10                  15 cag acc gac agc gtg gtg gcc acc ctg aag gcc tcc tac ccc ggc ctg      96
Gln Thr Asp Ser Val Val Ala Thr Leu Lys Ala Ser Tyr Pro Gly Leu
                20                  25                  30 cag ttc gag atc att gcc atg agc acc acc ggc gac aag atc ctg gac     144
Gln Phe Glu Ile Ile Ala Met Ser Thr Thr Gly Asp Lys Ile Leu Asp
            35                  40                  45 acc gcc ctg agc aag atc ggc gag aag agc ctg ttc aca aaa gag ctg     192
Thr Ala Leu Ser Lys Ile Gly Glu Lys Ser Leu Phe Thr Lys Glu Leu
        50                  55                  60 gaa cac gcc ctg gaa aag aac gag gtg gac ctg gtg gtg cac agc ctg     240
Glu His Ala Leu Glu Lys Asn Glu Val Asp Leu Val Val His Ser Leu
65                  70                  75                  80 aag gac ctg ccc acc gtg ctg ccc cct ggc ttc acc atc ggc gcc atc     288
Lys Asp Leu Pro Thr Val Leu Pro Pro Gly Phe Thr Ile Gly Ala Ile
                85                  90                  95 tgc aag aga gag aac ccc cac gac gcc gtg gtg ttc cac cct aag ttc     336
Cys Lys Arg Glu Asn Pro His Asp Ala Val Val Phe His Pro Lys Phe
            100                 105                 110 gtg ggc aag aca ctg gaa acc ctg ccc gag aag tcc gtg gtg ggc acc     384
Val Gly Lys Thr Leu Glu Thr Leu Pro Glu Lys Ser Val Val Gly Thr
        115                 120                 125 agc agc ctg cgg aga gcc gcc cag ctg cag cgg aag ttc ccc cac ctg     432
Ser Ser Leu Arg Arg Ala Ala Gln Leu Gln Arg Lys Phe Pro His Leu
    130                 135                 140 gaa ttt cgg agc atc cgg ggc aac ctg aac acc cgg ctg cgg aag ctg     480
Glu Phe Arg Ser Ile Arg Gly Asn Leu Asn Thr Arg Leu Arg Lys Leu
145                 150                 155                 160
```

-continued

| | | |
|---|---|---|
| gac gag cag cag gaa ttt tcc gct atc atc ctg gcc aca gcc gga ctg<br>Asp Glu Gln Gln Glu Phe Ser Ala Ile Ile Leu Ala Thr Ala Gly Leu<br>                              165                       170                   175 | | 528 |
| cag cgg atg ggc tgg cac aac aga gtg ggc cag atc ctg cac ccc gag<br>Gln Arg Met Gly Trp His Asn Arg Val Gly Gln Ile Leu His Pro Glu<br>           180                       185                       190 | | 576 |
| gaa tgc atg tac gcc gtg ggc cag gga gcc ctg ggc gtg gaa gtg cgg<br>Glu Cys Met Tyr Ala Val Gly Gln Gly Ala Leu Gly Val Glu Val Arg<br>                 195                       200                       205 | | 624 |
| gcc aag gac cag gac atc ctg gat ctg gtg ggc gtg ctg cat gac ccc<br>Ala Lys Asp Gln Asp Ile Leu Asp Leu Val Gly Val Leu His Asp Pro<br>210                       215                       220 | | 672 |
| gag aca ctg ctg cgg tgt atc gcc gag cgg gcc ttc ctg cgg cac ctg<br>Glu Thr Leu Leu Arg Cys Ile Ala Glu Arg Ala Phe Leu Arg His Leu<br>225                       230                       235                   240 | | 720 |
| gaa ggc ggc tgc agc gtg ccc gtg gcc gtg cac acc gcc atg aag gac<br>Glu Gly Gly Cys Ser Val Pro Val Ala Val His Thr Ala Met Lys Asp<br>                             245                       250                   255 | | 768 |
| gga cag ctg tac ctg aca ggc ggc gtg tgg agc ctg gac ggc agc gac<br>Gly Gln Leu Tyr Leu Thr Gly Gly Val Trp Ser Leu Asp Gly Ser Asp<br>                 260                       265                       270 | | 816 |
| agc atc cag gag acc atg cag gcc acc atc cac gtg ccc gcc cag cac<br>Ser Ile Gln Glu Thr Met Gln Ala Thr Ile His Val Pro Ala Gln His<br>           275                       280                       285 | | 864 |
| gag gac ggc ccc gag gac gac cct cag ctg gtc ggc atc acc gcc cgg<br>Glu Asp Gly Pro Glu Asp Asp Pro Gln Leu Val Gly Ile Thr Ala Arg<br>                 290                       295                       300 | | 912 |
| aac atc ccc aga ggc ccc cag ctg gcc gcc cag aac ctg ggc atc agc<br>Asn Ile Pro Arg Gly Pro Gln Leu Ala Ala Gln Asn Leu Gly Ile Ser<br>305                       310                       315                   320 | | 960 |
| ctg gcc aac ctg ctg ctg tcc aag ggc gcc aag aac atc ctg gac gtg<br>Leu Ala Asn Leu Leu Leu Ser Lys Gly Ala Lys Asn Ile Leu Asp Val<br>                       325                       330                   335 | | 1008 |
| gcc cgg cag ctg aac gac gcc cac tgatga<br>Ala Arg Gln Leu Asn Asp Ala His<br>               340 | | 1038 |

<210> SEQ ID NO 4
<211> LENGTH: 344
<212> TYPE: PRT
<213> ORGANISM: Artificial
<220> FEATURE:
<223> OTHER INFORMATION: Synthetic Construct

<400> SEQUENCE: 4

Met Arg Val Ile Arg Val Gly Thr Arg Lys Ser Gln Leu Ala Arg Ile
1               5                   10                  15

Gln Thr Asp Ser Val Val Ala Thr Leu Lys Ala Ser Tyr Pro Gly Leu
            20                  25                  30

Gln Phe Glu Ile Ile Ala Met Ser Thr Thr Gly Asp Lys Ile Leu Asp
        35                  40                  45

Thr Ala Leu Ser Lys Ile Gly Glu Lys Ser Leu Phe Thr Lys Glu Leu
    50                  55                  60

Glu His Ala Leu Glu Lys Asn Glu Val Asp Leu Val Val His Ser Leu
65                  70                  75                  80

Lys Asp Leu Pro Thr Val Leu Pro Pro Gly Phe Thr Ile Gly Ala Ile
                85                  90                  95

Cys Lys Arg Glu Asn Pro His Asp Ala Val Val Phe His Pro Lys Phe
            100                 105                 110

```
Val Gly Lys Thr Leu Glu Thr Leu Pro Glu Lys Ser Val Val Gly Thr
            115                 120                 125
Ser Ser Leu Arg Arg Ala Ala Gln Leu Gln Arg Lys Phe Pro His Leu
    130                 135                 140
Glu Phe Arg Ser Ile Arg Gly Asn Leu Asn Thr Arg Leu Arg Lys Leu
145                 150                 155                 160
Asp Glu Gln Gln Glu Phe Ser Ala Ile Ile Leu Ala Thr Ala Gly Leu
                165                 170                 175
Gln Arg Met Gly Trp His Asn Arg Val Gly Gln Ile Leu His Pro Glu
            180                 185                 190
Glu Cys Met Tyr Ala Val Gly Gln Gly Ala Leu Gly Val Glu Val Arg
        195                 200                 205
Ala Lys Asp Gln Asp Ile Leu Asp Leu Val Gly Val Leu His Asp Pro
    210                 215                 220
Glu Thr Leu Leu Arg Cys Ile Ala Glu Arg Ala Phe Leu Arg His Leu
225                 230                 235                 240
Glu Gly Gly Cys Ser Val Pro Val Ala Val His Thr Ala Met Lys Asp
                245                 250                 255
Gly Gln Leu Tyr Leu Thr Gly Val Trp Ser Leu Asp Gly Ser Asp
            260                 265                 270
Ser Ile Gln Glu Thr Met Gln Ala Thr Ile His Val Pro Ala Gln His
    275                 280                 285
Glu Asp Gly Pro Glu Asp Asp Pro Gln Leu Val Gly Ile Thr Ala Arg
290                 295                 300
Asn Ile Pro Arg Gly Pro Gln Leu Ala Ala Gln Asn Leu Gly Ile Ser
305                 310                 315                 320
Leu Ala Asn Leu Leu Leu Ser Lys Gly Ala Lys Asn Ile Leu Asp Val
                325                 330                 335
Ala Arg Gln Leu Asn Asp Ala His
            340
```

<210> SEQ ID NO 5
<211> LENGTH: 673
<212> TYPE: DNA
<213> ORGANISM: Artificial
<220> FEATURE:
<223> OTHER INFORMATION: Human AAT promoter combined with the mouse
      albumin gene enhancer (Ealb) element

<400> SEQUENCE: 5

```
tcgaggttcc tagattacac tacacattct gcaagcatag cacagagcaa tgttctactt     60
taattacttt cattttcttg tatcctcaca gcctagaaaa taacctgcgt tacagcatcc    120
actcagtatc ccttgagcat gaggtgacac tacttaacat agggacgaga tggtactttg    180
tgtctcctgc tctgtcagca gggcacagta cttgctgata ccagggaatg tttgttctta    240
aataccatca ttccggacgt gtttgccttg ccagttttc catgtacatg cagaaagaag     300
tttggactga tcaatacagt cctctgcctt taaagcaata ggaaaaggcc aacttgtcta    360
cgtttagtat gtggctgtag atctgtaccc gccaccccct ccaccttgga cacaggacgc    420
tgtggtttct gagccaggta caatgactcc tttcggtaag tgcagtggaa gctgtacact    480
gcccaggcaa agcgtccggg cagcgtaggc gggcgactca gatcccagcc agtggactta    540
gcccctgttt gctcctccga taactggggt gaccttggtt aatattcacc agcagcctcc    600
cccgttgccc ctctggatcc actgcttaaa tacggacgag acagggccc tgtctcctca     660
gcttcaggca cca                                                        673
```

<210> SEQ ID NO 6
<211> LENGTH: 69
<212> TYPE: DNA
<213> ORGANISM: Homo sapiens

<400> SEQUENCE: 6
gcctttgaat gtaaccaatc ctactaataa accagttctg aaggtgttgt gtgtgcgcgt    60
gtggagttg                                                           69

<210> SEQ ID NO 7
<211> LENGTH: 66
<212> TYPE: DNA
<213> ORGANISM: Artificial
<220> FEATURE:
<223> OTHER INFORMATION: synthetic polyA insulator

<400> SEQUENCE: 7
aattcaataa agagctctta ttttcattct cgaggtgtgg ttggttttct tgtgtggggg    60
cggatc                                                              66

<210> SEQ ID NO 8
<211> LENGTH: 10
<212> TYPE: RNA
<213> ORGANISM: Artificial
<220> FEATURE:
<223> OTHER INFORMATION: Kozak consensus sequence

<400> SEQUENCE: 8 gccrccauga                                                          10

<210> SEQ ID NO 9
<211> LENGTH: 145
<212> TYPE: DNA
<213> ORGANISM: adeno-associated virus 2

<400> SEQUENCE: 9
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcct                                         145

<210> SEQ ID NO 10
<211> LENGTH: 146
<212> TYPE: DNA
<213> ORGANISM: adeno-associated virus 2

<400> SEQUENCE: 10
ttggccactc cctctctgcg cgctcgctcg ctcactgagg ccgcccgggc aaagcccggg    60
cgtcgggcga cctttggtcg cccggcctca gtgagcgagc gagcgcgcag agagggagtg   120
gccaactcca tcactagggg ttcccc                                        146

PORPHOBILINOGEN DEAMINASE GENE THERAPY

FIELD OF THE INVENTION

The present invention relates to nucleotide sequences coding for human porphobilinogen deaminase and to nucleic acid constructs harbouring those sequences. The present invention further relates to novel gene therapy vectors and methods for their use in treating and preventing conditions caused by deficiency of porphobilinogen deaminase. More specifically, the gene therapy vectors of the invention may be used in methods of alleviating the symptoms of such conditions, including acute intermittent porphyria.

BACKGROUND OF THE INVENTION

Acute intermittent porphyria (AIP) is an inherited metabolic disease characterized by a deficiency of porphobilinogen deaminase (PBGD), the third enzyme of the heme synthesis pathway. The enzyme activity is ~50% of normal in those who inherit the genetic trait. The disease is inherited in an autosomal dominant manner and is the most common of acute porphyrias. Although it occurs in all races it is most prevalent in North Europe, mainly in Sweden, Britain and Ireland. In USA and other countries the estimated prevalence is 5/100,000 and in Northern Sweden it is as high as 60-100/100,000. More than 225 mutations in the PBGD gene have been described to date. The dominant clinical feature is an acute intermittent attack due to dysfunction of the nervous system, including abdominal pain and neurovisceral and circulatory disturbances. Abdominal pain has been reported in 85-95% of cases and is the most common feature, followed by or associated with the neurological changes. Progression to respiratory and bulbar paralysis and death may occur if AIP is not recognized and harmful drugs are not withdrawn, such as drugs metabolized by the hepatic cytochrome P450 enzymes which may precipitate an attack. Sudden death may also occur as result of cardiac arrhythmia. Primary liver cancer and impaired renal function sometimes occur as well.

An inherited deficiency of PBGD is not enough for the symptoms to appear. A high proportion of subjects that inherit PBGD mutation never develop porphyric symptoms, i.e. there is very low clinical penetrance. Clinical symptoms in AIP carriers are associated with increased production and excretion of the porphyrin precursors delta-aminolevulinic acid (ALA) and porphobilinogen (PBG) as result of increased demand of heme synthesis due to a drug or other precipitating factors that provoke the acute attack. In these conditions PBGD deficiency limits heme synthesis and as a result heme-mediated repression of ALA synthetase (ALAS1) is impaired. There is evidence indicating that the liver is the main source of the excess of porphyrin precursors. These compounds remain elevated between attacks in those subjects prone to repeated porphyric crises and increase further during the crisis. They may decrease to normal if the disease remains inactive for a long period of time.

Acute attacks usually occur after puberty and can be induced in latent individuals by endocrine factors and steroid hormones and a variety of environmental factors including drug, nutritional factors, restricted carbohydrate and caloric intake, smoking, steroid hormones and oral contraceptives, lead poisoning, intercurrent infections, surgery and psychological stress. Drugs are among the most important factors that precipitate acute attacks and a list of safe drugs is available in www.drugs-porphyria.com. Smoking, ethanol and drugs metabolized by CYP450, greatly increase hepatic heme demand and result in the induction of ALAS1, which increases the production of porphryin precursors and precipitates an acute attack. Also, ALAS1 is positively regulated by the peroxisome proliferator-activated receptor γ coactivator 1α (PGC1α), which is induced in the liver during fasting. Among the precipitating factors steroid hormones seem to play an important role. This concept is supported by the fact that the disease rarely manifests before puberty and that oral contraceptives can exacerbate attacks in some females with PBGD deficiency. Also women (80%) are affected more often than men (20%).

Acute attacks are treated with infusions of glucose and hemin (Normosang, Orphan Europe). Glucose appears to antagonize the ALAS1 induction mediated by PGC-1α. Hemin restores the regulatory heme pool and suppresses hepatic ALAS1 induction. Some women develop premenstrual attacks which can be prevented by gonadotropin-releasing hormone (GnRH) analogs. Some patients exhibit recurrent acute attacks and significant, disabling neurological dysfunction. Advanced neurologic damage and subacute and chronic symptoms are generally unresponsive to heme therapy. This is a life-threatening condition that can be cured only by allogeneic liver transplantation that, in three patients to date, prevents the accumulation of neurotoxic ALA and PBG. Nevertheless liver transplantation has limited availability of compatible donors, and a significant morbidity and mortality.

Thus, gene-replacement therapy is a potential alternative to liver transplantation in these patients where the liver function is entirely normal except for the PBGD deficiency. Gene therapy is a procedure consisting of the introduction of a specific gene into cells to control disease through the use of vectors. The feasibility of gene delivery therapies aiming to correct the hepatic enzyme defect are being explored in experimental models of AIP (AIP mice). Adenoviral vector-mediated gene transfer of PBGD to porphyric mice revealed short-term therapeutically efficacy as a result of the transient hepatic expression of PBGD (Johansson, 2004, Mol. Ther. 10(2):337-43). These results established a proof-of-principle, demonstrating that viral vector-mediated PBGD gene delivery may transiently ameliorate the severe manifestations of phenobarbital-induced porphyric attacks in AIP mice.

EP 1 049 487 discloses the construction of rAAV vectors containing a human PBGD cDNA only at a conceptual level.

There is however still a need in the art for improved vectors and protocols for AAV-mediated delivery of hPBGD to subjects in need thereof.

SUMMARY OF THE INVENTION

According to the invention, there is provided a nucleotide sequence, i.e. a nucleic acid or polynucleotide, coding for a human porphobilinogen deaminase (PBGD), wherein at least about 320 of the codons coding for the human porphobilinogen deaminase are identical to the codons in SEQ ID NO: 1 or wherein at least about 305 of the codons coding for the human porphobilinogen deaminase are identical to the codons in SEQ ID NO: 3. Preferably, the nucleotide sequence coding for the human porphobilinogen deaminase has at least 95% identity over the entire length of SEQ ID NO: 1 or 3, as determined by a Needleman and Wunsch global alignment algorithm.

The "codons" in SEQ ID NOs: 1 and 3 refer to the codons in the frame beginning with nucleotide 1 of SEQ ID NOs: 1 and 3, i.e. not the frame beginning with nucleotide 2 or 3 of SEQ ID NOs: 1 and 3. That is to say, the first codon of SEQ ID NOs: 1 and 3 is indicated by nucleotide numbers 1 to 3.

In another aspect, the invention relates to a nucleic acid construct comprising a nucleotide sequence coding for a human porphobilinogen deaminase, wherein at least about 320 of the codons coding for the human porphobilinogen deaminase are identical to the codons in SEQ ID NO: 1 or wherein at least about 305 of the codons coding for the human porphobilinogen deaminase are identical to the codons in SEQ ID NO: 3. Preferably, in the nucleic acid construct the nucleotide sequence coding for the human porphobilinogen deaminase is operably linked to a promoter for expression in human cells, preferably a liver-specific promoter.

In a further aspect the invention relates to viral gene therapy vector comprising the nucleotide sequence coding for the human porphobilinogen deaminase operably linked to a promoter for expression in human cells. Preferably, the vector is a recombinant parvoviral or adeno-associated viral (AAV) vector.

In a further aspect, the invention pertains to a nucleic acid, nucleic acid construct or parvoviral virion comprising the recombinant parvoviral or AAV vector that comprises the nucleotide sequence coding for the human porphobilinogen deaminase.

In yet a further aspect, the invention relates to a pharmaceutical composition comprising such a nucleic acid, nucleic acid construct or parvoviral virion and a pharmaceutically acceptable carrier.

Further aspects of the invention relate to these nucleic acids, nucleic acid constructs or parvoviral virions for use as a medicament, and for use in the treatment of a condition caused by a deficiency in porphobilinogen deaminase, wherein, preferably the condition is acute intermittent porphyria (AIP).

The invention also relates to use of a nucleic acid, nucleic acid construct or parvoviral virion of the invention for use in the manufacture of a medicament for use in the treatment of a condition caused by a deficiency in porphobilinogen deaminase.

Also provided is a method for the delivery of a nucleotide sequence encoding porphobilinogen deaminase to a mammal which method comprises:
a. providing a nucleic acid, nucleic acid construct or parvoviral virion of the invention; and
b. administering said nucleic acid, nucleic acid construct or parvoviral virion to a mammal under conditions that result in the expression of protein at a level that provides a therapeutic effect in said mammal.

The invention also relates to a method for treating a condition caused by a deficiency in porphobilinogen deaminase wherein the method comprises the step of administering an effective amount of a pharmaceutical composition comprising a nucleic acid, nucleic acid construct or parvoviral virion with the nucleotide sequence coding for the human porphobilinogen deaminase, to a subject with a porphobilinogen deaminase deficiency, wherein, preferably the condition is acute intermittent porphyria.

DESCRIPTION OF THE INVENTION

Definitions

A "nucleic acid" includes any molecule composed of or comprising monomeric nucleotides. The term "nucleotide sequence" may be used interchangeably with "nucleic acid" herein. A nucleic acid may be an oligonucleotide or a polynucleotide. A nucleic acid may be a DNA or an RNA. A nucleic acid may be chemically modified or artificial. Artificial nucleic acids include peptide nucleic acid (PNA), Morpholino and locked nucleic acid (LNA), as well as glycol nucleic acid (GNA) and threose nucleic acid (TNA). Each of these is distinguished from naturally-occurring DNA or RNA by changes to the backbone of the molecule. Also, phosphorothioate nucleotides may be used. Other deoxynucleotide analogs include methylphosphonates, phosphoramidates, phosphorodithioates, N3'P5'-phosphoramidates and oligoribonucleotide phosphorothioates and their 2'-O-allyl analogs and 2'-O-methylribonucleotide methylphosphonates which may be used in a nucleic acid of the invention.

A "nucleic acid construct" is herein understood to mean a man-made nucleic acid molecule resulting from the use of recombinant DNA technology. A nucleic acid construct is a nucleic acid molecule, either single- or double-stranded, which has been modified to contain segments of nucleic acids, which are combined and juxtaposed in a manner, which would not otherwise exist in nature. A nucleic acid construct usually is a "vector", i.e. a nucleic acid molecule which is used to deliver exogenously created DNA into a host cell.

One type of nucleic acid construct is an "expression cassette" or "expression vector". These terms refers to nucleotide sequences that are capable of effecting expression of a gene in host cells or host organisms compatible with such sequences. Expression cassettes or expression vectors typically include at least suitable transcription regulatory sequences and optionally, 3' transcription termination signals. Additional factors necessary or helpful in effecting expression may also be present, such as expression enhancer elements.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species. The term "heterologous" may be used to indicate that in nature the nucleic acid or polypeptide molecule is produced by a host cell or organisms of a different species.

As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signals for introns, and stop codons. The term "expression control sequence" is intended to include, at a minimum, a sequence whose presence are designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, which may be referred to as polyA sequences. It also can be designed to enhance mRNA stability. Expression control sequences which affect the transcription and translation stability, e.g., promoters, as well as sequences which effect the translation, e.g., Kozak sequences, suitable for use in insect cells are well known to those skilled in the art. Expression control sequences can be of such nature as to modulate the nucleotide sequence to which it is operably linked such that lower expression levels or higher expression levels are achieved.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter, including e.g. attenuators or enhancers, but also silencers. A "constitutive" promoter is a promoter that is active in most tissues under most physiological and developmental conditions. An "inducible" promoter is a promoter that is physiologically or developmentally regulated, e.g. by the application of a chemical inducer. A "tissue specific" promoter is only active in specific types of tissues or cells.

A "3' UTR" or "3' non-translated sequence" (also often referred to as 3' untranslated region, or 3'end) refers to the nucleic acid sequence found downstream of the coding sequence of a gene, which comprises, for example, a transcription termination site and (in most, but not all eukaryotic mRNAs) a polyadenylation signal (such as e.g. AAUAAA or variants thereof). After termination of transcription, the mRNA transcript may be cleaved downstream of the polyadenylation signal and a poly(A) tail may be added, which is involved in the transport of the mRNA to the cytoplasm (where translation takes place).

The terms "substantially identical", "substantial identity" or "essentially similar" or "essential similarity" means that two peptide or two nucleotide sequences, when optimally aligned, such as by the programs GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). It is clear than when RNA sequences are said to be essentially similar or have a certain degree of sequence identity with DNA sequences, thymine (T) in the DNA sequence is considered equal to uracil (U) in the RNA sequence. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or the open-source software Emboss for Windows (current version 2.7.1-07). Alternatively percent similarity or identity may be determined by searching against databases such as FASTA, BLAST, etc.

In this document and in its claims, the verb "to comprise" and its conjugations are used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

DETAILED DESCRIPTION OF THE INVENTION

The invention pertains to a nucleotide sequences coding for porphobilinogen deaminase. The nucleotide sequence coding for porphobilinogen deaminase is preferably a synthetic nucleotide sequence. The term "synthetic nucleotide sequence" is herein understood to mean that the nucleotide sequence does not occur as such in nature, but rather was designed, engineered and/or constructed by human intervention. The term "synthetic" thus does not necessarily imply that the sequence is exclusively and/or entirely obtained through chemical synthesis. Rather, although parts of the synthetic sequence may at one stage have been obtained through chemical synthesis, molecules comprising a synthetic sequence of the invention will usually be obtained from biological sources such as (cultured, for example recombinant) cells.

The nucleotide sequence of the invention may encode an erythroid or a non-erythroid porphobilinogen deaminase. Preferably, the nucleotide sequence encodes a porphobilinogen deaminase of human origin. The nucleotide sequence may thus encode any naturally occurring amino acid sequence of an allelic form of a human porphobilinogen deaminase. However, explicitly included in the inventions are nucleotide sequence that encode engineered muteins of porphobilinogen deaminases having one more amino acid substitutions, deletions and/or insertions compared to e.g. a naturally occurring human amino acid sequence. Preferably the nucleotide sequence encodes a protein that has porphobilinogen deaminase activity (EC 2.5.1.61) as may be determined by an assay as e.g. described by Wright and Lim (1983, Biochem. J. 213: 85-88).

In a preferred embodiment of the invention, the nucleotide sequence coding for a porphobilinogen deaminase has an improved codon usage bias for the human cell as compared to naturally occurring nucleotide sequence coding for the deaminases. The adaptiveness of a nucleotide sequence encoding a porphobilinogen deaminase to the codon usage of human cells may be expressed as codon adaptation index (CAI). A codon adaptation index is herein defined as a measurement of the relative adaptiveness of the codon usage of a gene towards the codon usage of highly expressed human genes. The relative adaptiveness (w) of each codon is the ratio of the usage of each codon, to that of the most abundant codon for the same amino acid. The CAI is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Kim et al., Gene. 1997, 199:293-301; zur Megede et al., Journal of Virology, 2000, 74: 2628-2635). Preferably, a nucleotide sequence encoding a porphobilinogen deaminase has a CAI of at least 0.8, 0.85, 0.90, 0.92, 0.94, 0.95, 0.96 or 0.97.

In a preferred nucleotide sequence of the invention, at least 320, 330, 340, 345, 350, 355, 356, 357, 358, 359, 360, or 361 of all codons coding for the non-erythroid porphobilinogen deaminase are identical to the codons (in corresponding positions) in SEQ ID NO: 1. More preferably the nucleotide sequence codes for the amino acid sequence of SEQ ID NO: 2.

Alternatively, in a preferred nucleotide sequence of the invention, at least 305, 310, 315, 320, 325, 330, 335, 340, 341, 342, 343, or 344 of the codons coding for the erythroid porphobilinogen deaminase are identical to the codons (in corresponding positions) in SEQ ID NO: 3. More preferably the nucleotide sequence codes for the amino acid sequence of SEQ ID NO: 4.

The "codons" in SEQ ID NOs: 1 and 3 refer to the codons in the frame beginning with nucleotide 1 of SEQ ID NOs: 1 and 3, i.e. not the frame beginning with nucleotide 2 or 3 of SEQ ID NOs: 1 and 3. That is to say, the first codon of SEQ NOs: 1 and 3 is indicated by nucleotide numbers 1 to 3.

Another preferred nucleotide sequence of the invention codes for a polypeptide with porphobilinogen deaminase activity, whereby the nucleotide sequence has at least 95, 96, 97, 98 or 99% nucleotide sequence identity over its entire length with SEQ ID NO: 1 or 3, as determined by a Needleman and Wunsch global alignment algorithm. More preferably the nucleotide sequence codes for the amino acid sequences of SEQ ID NO: 2 or 4.

In a particularly preferred embodiment of invention, the nucleotide sequence has the nucleotide sequence of SEQ ID NO: 1 or 3.

In a further aspect the invention pertains to a nucleic acid construct comprising a nucleotide sequence of the invention as herein defined above. In the nucleic acid construct the nucleotide sequence encoding the porphobilinogen deaminase preferably is operably linked to a mammalian cell-compatible expression control sequence, e.g., a promoter. Many such promoters are known in the art (see Sambrook and Russell, 2001, supra). Constitutive promoters that are broadly expressed in many cell types, such as the CMV promoter may be used. However, promoters that are inducible, tissue-specific, cell-type-specific, or cell cycle-specific may be preferred. In a preferred embodiment, the nucleotide sequence encoding the porphobilinogen deaminase is operably linked to a liver-specific promoter. Liver-specific promoters are particularly preferred for use in conjunction the non-erythroid deaminase. Preferably, in a construct of the invention an expression control sequence for liver-specific expression are e.g. selected from the group consisting of an α1-anti-trypsin (AAT) promoter, a thyroid hormone-binding globulin promoter, an albumin promoter, a thyroxin-binding globulin (TBG) promoter, an Hepatic Control Region (HCR)-ApoCII hybrid promoter, an HCR-hAAT hybrid promoter, an AAT promoter combined with the mouse albumin gene enhancer (Ealb) element and an apolipoprotein E promoter. Other examples include the E2F promoter for tumour-selective, and, in particular, neurological cell tumour-selective expression (Parr et al., 1997, Nat. Med. 3:1145-9) or the IL-2 promoter for use in mononuclear blood cells (Hagenbaugh et al., 1997, J Exp Med; 185: 2101-10). In a particularly preferred embodiment of the invention, wherein the promoter has the sequence of SEQ ID NO: 5.

In a further preferred embodiment of the nucleic acid construct of the invention a 3'UTR (or 3' non-translated sequence) may be located downstream of the nucleotide sequence encoding the porphobilinogen deaminase. Suitable 3'UTR sequences are available to the skilled person. They may be derived from any mammalian and preferably human gene and will usually comprise a transcription termination site and a polyadenylation signal (such as e.g. AAUAAA or variants thereof). In a particularly preferred embodiment the nucleic acid construct comprises a 3'UTR derived from the human PBGD gene such as e.g. SEQ ID NO: 6.

In another preferred embodiment of the nucleic acid construct of the invention, the expression control sequence that is operably linked to the nucleotide sequence encoding the porphobilinogen deaminase, is preceded upstream by a polyA insulator to terminate run-through transcription from possible upstream transcription units. A 3'UTR as described above and preferably at least comprising a transcription termination sequence may be used for this purpose. A preferred polyA insulator is a synthetic polyA insulator having the sequence of SEQ ID NO: 7.

In one preferred embodiment the nucleic acid construct, the invention may comprise a Kozak consensus sequence around the initiation codon of the nucleotide sequence encoding the porphobilinogen deaminase. The Kozak consensus sequence is herein defined as GCCRCC(AUG)A (SEQ ID NO: 8), wherein R is a purine (i.e. A, adenosine or G, guanosine) and wherein (AUG) stands for the initiation codon of the porphobilinogen deaminase coding sequence. Although in the usual Kozak consensus sequence the nucleotide directly following the AUG initiation codon is a G (guanosine), in context of the present invention this nucleotide preferably is an A (adenosine) in both the erythroid and non-erythroid porphobilinogen deaminase coding sequence. In a preferred embodiment the Kozak consensus sequence may be preceded by another GCC triplet.

In an additional aspect the invention relates to a nucleic acid construct comprising a nucleotide sequence encoding the porphobilinogen deaminase that is operably linked to an expression control sequence as defined herein above, wherein the construct is an expression vector that is suitable for gene therapy of mammals, preferably gene therapy of humans. A preferred nucleic acid construct according to the invention is a viral gene therapy vector. Viral gene therapy vectors are well known in the art and e.g. include vectors based on an adenovirus, and members of the Parvoviridae family, such as an adeno-associated virus (AAV), or a herpes virus, pox virus or retrovirus. A preferred viral gene therapy vector is an AAV, adenoviral or a lentiviral vector.

Particularly preferred gene therapy vectors in the context of the present invention are parvoviral vectors. Thus, in this preferred aspect the invention relates the use of animal parvoviruses, in particular *dependoviruses* such as infectious human or simian AAV, and the components thereof (e.g., an animal parvovirus genome) for use as vectors for introduction and/or expression of the nucleotide sequences encoding a porphobilinogen deaminase in mammalian cells.

Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus *Dependovirus*. As may be deduced from the name of their genus, members of the *Dependovirus* are unique in that they usually require co-infection with a helper virus such as adenovirus or herpes virus for productive infection in cell culture. The genus *Dependovirus* includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience the present invention is further exemplified and described herein by reference to AAV. It is however understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wild-type (wt) AAV infection in mammalian cells the Rep genes (i.e. Rep78 and Rep52) are expressed from the P5 promoter and the P19 promoter, respectively and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

A "recombinant parvoviral or AAV vector" (or "rAAV vector") herein refers to a vector comprising one or more polynucleotide sequences of interest, genes of interest or "transgenes" that are flanked by at least one parvoviral or AAV inverted terminal repeat sequences (ITRs). Such rAAV vectors can be replicated and packaged into infectious viral particles when present in an insect host cell that is expressing AAV rep and cap gene products (i.e. AAV Rep and Cap proteins). When an rAAV vector is incorporated into a larger nucleic acid construct (e.g. in a chromosome or in another vector such as a plasmid or baculovirus used for cloning or transfection), then the rAAV vector is typically referred to as a "pro-vector" which can be "rescued" by replication and encapsidation in the presence of AAV packaging functions and necessary helper functions. Thus, in a further aspect the invention relates to a nucleic acid construct comprising a nucleotide sequence encoding a porphobilinogen deaminase as herein defined above, wherein the nucleic acid construct is a recombinant parvoviral or AAV vector and thus comprises at least one parvoviral or AAV ITR. Preferably, in the nucleic acid construct the nucleotide sequence encoding the porphobilinogen deaminase is flanked by parvoviral or AAV ITRs on either side. Any parvoviral or AAV ITR may be used in the constructs of the invention, including ITRs from AAV1, AAV2, AAV4, AAV5, AAV6, AAV8 and/or AAV9. ITRs of AAV2 are most preferred. Examples of preferred ITR sequences for use in preferred nucleic acid constructs of the invention are given SEQ ID NO: 9 (left or upstream ITR) and SEQ ID NO: 10 (right or downstream ITR).

AAV is able to infect a number of mammalian cells. See, e.g., Tratschin et al. (1985, Mol. Cell Biol. 5:3251-3260) and Grimm et al. (1999, Hum. Gene Ther. 10:2445-2450). However, AAV transduction of human synovial fibroblasts is significantly more efficient than in similar murine cells, Jennings et al., Arthritis Res, 3:1 (2001), and the cellular tropicity of AAV differs among serotypes. See, e.g., Davidson et al. (2000, Proc. Natl. Acad. Sci. USA, 97:3428-3432), who discuss differences among AAV2, AAV4, and AAV5 with respect to mammalian CNS cell tropism and transduction efficiency and see Goncalves, 2005, Virol J. 2(1):43 who discusses approaches to modification of AAV tropism. For transduction of liver cells rAAV virions with AAV1, AAV8 and AAV5 capsid proteins are preferred (Nathwani et al., 2007, Blood 109(4): 1414-1421; Kitajima et al., 2006, Atherosclerosis 186(1):65-73), of which is rAAV virions with AAV5 capsid proteins may be most preferred.

AAV sequences that may be used in the present invention for the production of rAAV vectors in insect cells can be derived from the genome of any AAV serotype. Generally, the AAV serotypes have genomic sequences of significant homology at the amino acid and the nucleic acid levels. This provides an identical set of genetic functions to produce virions which are essentially physically and functionally equivalent. For the genomic sequence of the various AAV serotypes and an overview of the genomic similarities see e.g. GenBank Accession number U89790; GenBank Accession number J01901; GenBank Accession number AF043303; GenBank Accession number AF085716; Chlorini et al. (1997, J. Vir. 71: 6823-33); Srivastava et al. (1983, J. Vir. 45:555-64); Chlorini et al. (1999, J. Vir. 73:1309-1319); Rutledge et al. (1998, J. Vir. 72:309-319); and Wu et al. (2000, J. Vir. 74: 8635-47). rAAV serotypes 1, 2, 3, 4 and 5 are preferred source of AAV nucleotide sequences for use in the context of the present invention. Preferably the AAV ITR sequences for use in the context of the present invention are derived from AAV1, AAV2, and/or AAV4. Likewise, the Rep (Rep78/68 and Rep52/40) coding sequences are preferably derived from AAV1, AAV2, and/or AAV4. The sequences coding for the viral proteins (VP) VP1, VP2, and VP3 capsid proteins for use in the context of the present invention may however be taken from any of the known 42 serotypes, more preferably from AAV1, AAV2, AAV3, AAV4, AAV5, AAV6, AAV7, AAV8 or AAV9 or newly developed AAV-like particles obtained by e.g. capsid shuffling techniques and AAV capsid libraries.

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82% (Bantel-Schaal et al., 1999, J. Virol., 73(2):939-947). Moreover, the Rep sequences and ITRs of many AAV serotypes are known to efficiently cross-complement (i.e., functionally substitute) corresponding sequences from other serotypes in production of AAV particles in mammalian cells. US2003148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability of Rep and ITR sequences to cross-complement corresponding sequences of other serotypes allows for the production of pseudotyped rAAV particles comprising the capsid proteins of one serotype (e.g., AAV5) and the Rep and/or ITR sequences of another AAV serotype (e.g., AAV2). Such pseudotyped rAAV particles are a part of the present invention. Herein, a pseudotyped rAAV particle may be referred to as being of the type "x/y", where "x" indicates the source of ITRs and "y" indicates the serotype of capsid, for example a 2/5 rAAV particle has ITRs from AAV2 and a capsid from AAV5.

Modified "AAV" sequences also can be used in the context of the present invention, e.g. for the production of rAAV vectors in insect cells. Such modified sequences e.g. include sequences having at least about 70%, at least about 75%, at least about 80%, at least about 85%, at least about 90%, at least about 95%, or more nucleotide and/or amino acid sequence identity (e.g., a sequence having from about 75% to about 99% nucleotide sequence identity) to an AAV1, AAV2, AAV3, AAV4, AAV5, AAV6, AAV7, AAV8 or AAV9 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. In view thereof, the production of rAAV5 can differ from production of other serotypes in insect cells. Where methods of the invention are employed to produce rAAV5, it is preferred that one or more constructs comprising, collectively in the case of more than one construct, a nucleotide sequence comprising an AAV5 ITR, a nucleotide sequence comprises an AAV5 Rep coding sequence (i.e. a nucleotide sequence comprises an AAV5 Rep78). Such ITR and Rep sequences can be modified as desired to obtain efficient production of rAAV5 or pseudotyped rAAV5 vectors in insect cells. E.g., the start codon of the Rep sequences can be modified, VP splice sites can be modified or eliminated, and/or the VP1 start codon and nearby nucleotides can be modified to improve the production of rAAV5 vectors in the insect cell.

Preferred adenoviral vectors are modified to reduce the host response as reviewed by Russell (2000, J. Gen. Virol. 81: 2573-2604), or as described in US20080008690 and by Zaldumbide and Hoeben (Gene Therapy 2008:239-246).

The invention thus also relates to a parvoviral virion comprising a nucleic acid construct as herein defined above, and parvoviral capsid protein as defined herein above.

In an additional aspect, the invention relates to a method for producing a recombinant parvoviral (for example rAAV) virion (comprising a recombinant parvoviral (rAAV) vector as defined above) in an insect cell. Preferably, the method comprises the steps of: (a) culturing an insect cell as defined herein under conditions such that recombinant parvoviral (for example rAAV) vector is produced; and, (b) recovery of the recombinant parvoviral (for example rAAV) vector. It is understood here that the recombinant parvoviral (rAAV) vector produced in the method preferably is an infectious parvoviral or AAV virion that comprise the recombinant parvoviral (rAAV) vector nucleic acids. Growing conditions for insect cells in culture, and production of heterologous products in insect cells in culture are well-known in the art and described e.g. in the above cited references on molecular engineering of insects cells. Preferred methods and constructs for the production of rAAV virions of the invention are disclosed in e.g. WO2007/046703 and WO2007/148971.

Preferably the method for producing recombinant parvoviral virions further comprises the step of affinity-purification of the (virions comprising the) recombinant parvoviral (rAAV) vector using an anti-AAV antibody, preferably an immobilised antibody. The anti-AAV antibody preferably is an monoclonal antibody. A particularly suitable antibody is a single chain camelid antibody or a fragment thereof as e.g. obtainable from camels or llamas (see e.g. Muyldermans, 2001, Biotechnol. 74: 277-302). The antibody for affinity-purification of rAAV preferably is an antibody that specifically binds an epitope on a AAV capsid protein, whereby preferably the epitope is an epitope that is present on capsid proteins of more than one AAV serotype. E.g. the antibody may be raised or selected on the basis of specific binding to AAV2 capsid but at the same time also it may also specifically bind to AAV1, AAV3 and AAV5 capsids.

Also, the invention pertains to a parvoviral virion as herein defined above, for use as a medicament. That is to say, the invention provides a parvoviral virion of the invention for use in the method of treatment of the human or animal body by therapy.

The invention further pertains to a parvoviral virion as herein defined above, for use in the treatment of a condition caused by a deficiency in porphobilinogen deaminase. Preferably such condition is acute intermittent porphyria. A nucleic acid or a nucleic acid construct of the invention are also suitable for such use.

Accordingly, the invention relates to a nucleic acid, a nucleic acid construct or a parvoviral virion of the invention for use in the preparation of medicament for use in a method of treatment of a condition caused by a deficiency in porphobilinogen deaminase. Preferably such condition is acute intermittent porphyria. Such treatment may alleviate, ameliorate, reduce the severity of one or more symptoms of AIP, for example reducing the incidence or severity of an attack. For example, treatment according to the invention may alleviate, ameliorate, reduce the severity of dysfunction of the nervous system, abdominal pain or neurovisceral and/or circulatory disturbances.

Further, the invention pertains to a pharmaceutical composition comprising a parvoviral virion as herein defined above. The pharmaceutical composition further preferably comprises a pharmaceutically acceptable carrier. Any suitable pharmaceutically acceptable carrier or excipient can be used in the present compositions (See e.g., Remington: The Science and Practice of Pharmacy, Alfonso R. Gennaro (Editor) Mack Publishing Company, April 1997). Preferred pharmaceutical forms would be in combination with sterile saline, dextrose solution, or buffered solution, or other pharmaceutically acceptable sterile fluids. Alternatively, a solid carrier, may be used such as, for example, microcarrier beads.

Pharmaceutical compositions are typically sterile and stable under the conditions of manufacture and storage. Pharmaceutical compositions may be formulated as a solution, microemulsion, liposome, or other ordered structure suitable to accommodate high drug concentration. The carrier may be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. The parvoviral virion may be administered in a time or controlled release formulation, for example in a composition which includes a slow release polymer or other carriers that will protect the compound against rapid release, including implants and microencapsulated delivery systems. Biodegradable, biocompatible polymers may for example be used, such as ethylene vinyl acetate, polyanhydrides, polyglycolic acid, collagen, polyorthoesters, polylactic acid and polylactic, polyglycolic copolymers (PLG).

The invention also provides a method for the delivery of a nucleotide sequence encoding porphobilinogen deaminase to a mammal which method comprises:

a. providing a nucleic acid, nucleic acid construct, parvoviral virion or pharmaceutical composition as defined herein; and b. administering said nucleic acid, nucleic acid construct, parvoviral virion or pharmaceutical composition to a mammal under conditions that result in the expression of protein at a level that provides a therapeutic effect in said mammal.

Also, the invention relates to a method for treating a condition caused by a deficiency in porphobilinogen deaminase wherein the method comprises the step of administering an effective amount of a nucleic acid, nucleic acid construct, parvoviral virion or pharmaceutical composition as defined herein above to a subject with a porphobilinogen deaminase deficiency. Preferably the subject is suffering from the condition acute intermittent porphyria.

In the treatment or therapy according to the invention, a condition caused by a deficiency in porphobilinogen deaminase is treated by administering to a subject an effective amount of a nucleic acid, nucleic acid construct, parvoviral virion or pharmaceutical composition as defined herein.

The condition of a patient suffering from a such a condition can be improved by administration of a nucleic acid, nucleic acid construct, parvoviral virion or pharmaceutical composition of the invention. A therapeutically effective amount of a nucleic acid, nucleic acid construct, parvoviral virion or pharmaceutical composition of the invention may be given to a patient in need thereof.

The a nucleic acid, nucleic acid construct, parvoviral virion or pharmaceutical composition will typically be included in a pharmaceutical composition, optionally in combination with a pharmaceutical carrier, diluent and/or adjuvant. Such compositions include the nucleic acid, nucleic acid construct, parvoviral virion or pharmaceutical composition in an effective amount, sufficient to provide a desired therapeutic or prophylactic effect, and a pharmaceutically acceptable carrier or excipient. An "effective amount" includes a therapeutically effective amount or a prophylactically effective amount.

A "therapeutically effective amount" refers to an amount effective, at dosages and for periods of time necessary, to achieve the desired therapeutic result, such as elevation of PBGD activity. A therapeutically effective amount of a nucleic acid, nucleic acid construct, parvoviral virion or pharmaceutical composition may vary according to factors such as the disease state, age, sex, and weight of the individual, and the ability of the nucleic acid, nucleic acid construct, parvoviral virion or pharmaceutical composition to elicit a desired response in the individual. Dosage regimens may be adjusted to provide the optimum therapeutic response. A therapeutically effective amount is also typically one in which any toxic or detrimental effects of the nucleic acid, nucleic acid construct, parvoviral virion or pharmaceutical composition are outweighed by the therapeutically beneficial effects.

A "prophylactically effective amount" refers to an amount effective, at dosages and for periods of time necessary, to achieve the desired prophylactic result, such as preventing or inhibiting various conditions, including a condition associated with a reduction in PBGD levels. A prophylactic dose may be used in subjects prior to or at an earlier stage of disease, and a prophylactically effective amount may be more or less than a therapeutically effective amount in some cases.

In particular embodiments, a range for therapeutically or prophylactically effective amounts of a nucleic acid, nucleic acid construct, parvoviral virion or pharmaceutical composition may be from $1\times10^{12}$ and $1\times10^{13}$ genome copy (gc)/kg, for example from $1\times10^{11}$ to $1\times10^{12}$ gc/kg. It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners.

For gene therapy vectors, such as the parvoviral virion of the present invention, the dosage to be administered may depend to a large extent on the condition and size of the subject being treated as well as the therapeutic formulation, frequency of treatment and the route of administration. Regimens for continuing therapy, including dose, formulation, and frequency may be guided by the initial response and clinical judgment. The parenteral route of injection into the interstitial space of tissue may be preferred, although other parenteral routes, such as inhalation of an aerosol formulation, may be required in specific administration. In some protocols, a formulation comprising the gene and gene delivery system in an aqueous carrier is injected into tissue in appropriate amounts.

The tissue target may be specific, for example the liver tissue, or it may be a combination of several tissues, for example the muscle and liver tissues. Exemplary tissue targets may include liver, skeletal muscle, heart muscle, adipose deposits, kidney, lung, vascular endothelium, epithelial and/or hematopoietic cells. In one embodiment, the effective dose range for small animals (mice), following intramuscular injection, may be between $1\times10^{12}$ and $1\times10^{13}$ genome copy (gc)/kg, and for larger animals (cats) and for human subjects, between $1\times10^{11}$ and $1\times10^{12}$ gc/kg.

The amount of active a nucleic acid, nucleic acid construct, parvoviral virion or pharmaceutical composition in the compositions of the invention may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation.

It may be advantageous to formulate parenteral compositions in dosage unit form for ease of administration and uniformity of dosage. "Dosage unit form" as used herein refers to physically discrete units suited as unitary dosages for subjects to be treated; each unit containing a predetermined quantity of active compound calculated to produce the desired therapeutic effect in association with the required pharmaceutical carrier. The specification for the dosage unit forms of the invention may be dictated by the unique characteristics of the active compound and the particular therapeutic effect to be achieved, and by the limitations inherent in the art of compounding such an active compound for the treatment of a condition in individuals.

As used herein "pharmaceutically acceptable carrier" or "exipient" includes any and all solvents, dispersion media, coatings, antibacterial and antifungal agents, isotonic and absorption delaying agents, and the like that are physiologically compatible. In one embodiment, the carrier is suitable for parenteral administration, which includes intravenous, intraperitoneal or intramuscular administration. Alternatively, the carrier may be suitable for sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated.

Supplementary active compounds can also be incorporated into the pharmaceutical compositions of the invention. Guidance on co-administration of additional therapeutics may for example be found in the Compendium of Pharmaceutical and Specialties (CPS) of the Canadian Pharmacists Association.

EXAMPLES

Example 1

Figure 1:
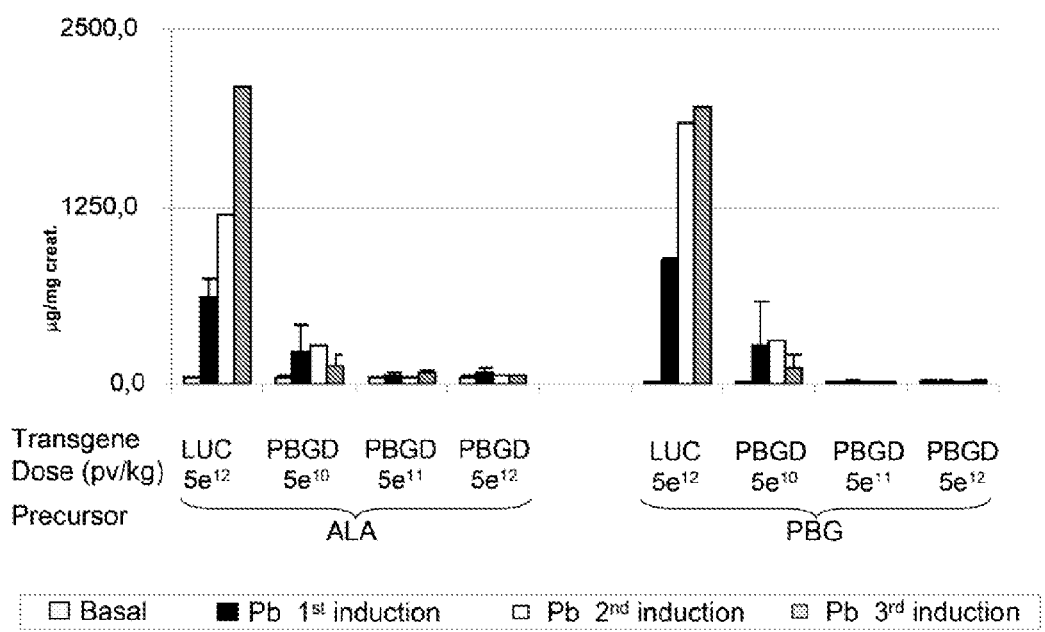
FIG. 1. Dose effect of AAV2/8-hPBGD injection on heme precursor excretion in male AIP mice. AIP mice have 25-30% of normal PBGD activity, resulting from a disruption in one allele of PBGD and a partial disruption in the other allele. LUC is luciferase reporter construct; PBGD is various doses of rAAV-PBGD vector. Expressed as genome copies per kilogram; Pb is phenobarbital.

AAV-Mediated Liver-Specific Expression of Porphobilinogen Deaminase Reverts Biochemical Alterations and Protects Against Motor Neuropathy in a Mouse Model of Acute Intermittent Porphyria 1.1 Materials and Methods.
1.1.1 Animal Model The acute intermittent porphyria (AIP) mice were generated by gene targeting as described by Lindberg et al. (Nature genetics, 1996). The T1 and T2 transgenic strains were kindly provided by Prof. Urs Meyer from the University of Basel and the animal facility of the University of Navarra has established a colony of these animals. In T1 transgenic animals a Neomycin gene has been inserted in the first exon of the PBGD gene and homozygous animal have a 45% loss of the PBGD activity in the liver. In T2 mice the Neomycin gene has been inserted in the first intron of the PBGD gene. Homozygous condition is lethal and heterozygotes animals exhibit a 43% loss of PBGD activity in the liver. Neither of the strains showed signs of porphyria nor increased urinary excretion of heme precursors after treatment with phenobarbital (Pb) and/or estradiol (data not shown). To further lower the PBGD activity, crossbreeding the two strains was performed. Compound heterozygotes animals, carrying knockout alleles for both T1 and T2 are used as a disease model for AIP. These mice exhibit the typical biochemical characteristics of human porphyria, notably, decreased hepatic PBGD activity and massively increased urinary excretion of heme precursors after treatment with drugs such as phenobarbital. Porphyrins, mostly uroporphyrin and coproporphyrin, are also elevated in AIP but increased urinary porphyrin is a much less specific feature than increases in PBG and ALA levels. Behavioural tests such as the rotarod test reveal decreased motor function after Pb administration and histopathological findings include axonal neuropathy and decreased nerve conduction with aging.

1.1.2 AAV Vector
Plasmids and Sequences

The AAV plasmids used in this study contain an expression cassette flanked by two ITRs from the AAV2 and an appropriate stuffer sequence to adjust the size of the AAV genome to the optimal packaging capacity described for AAV. The transgene expression cassette has the following elements: the 5'ITR from AAV2, a liver-specific promoter EalbAATp with regulatory sequences from the albumin enhancer (Kramer et al., 2003, Mol Ther. 7(3):375-85), the housekeeping PBGD cDNA (GenBank acc #X04808) or Luciferase reporter gene (GenBank acc #M15077). The bovine growth hormone polyadenylation sequence [bGH poly(A)] (bases 2326-2533 GenBank acc #M57764), a woodchuck hepatitis virus post-transcriptional regulatory element (WPRE) (bases 1021-1750 GenBank acc #J04514) was added to enhance transcription (Donello et al., 1998 J Virol. 72(6):5085-92) and the 3'ITR from AAV2. These two AAV plasmids were named ssAAV-polyA-EalbAAT-PBGD-WPRE (expressing the therapeutic gene) and ssAAV-polyA-EalbAAT-Luciferase-WPRE (expressing the reporter gene GFP).

Preparation of AAV Vectors

AAV2/8 vectors were produced by calcium phosphate-mediated co-transfection in 293 cells of three different plasmids pAdDeltaF6, p5E18-VD2/8 and the therapeutic (AAV-polyA-EalbAAT-PBGD-WPRE) or reporter gene (AAV-polyA-EalbAAT-Luciferase-WPRE), (Hermens et al, 1999 Hum Gene Ther. 10(11):1885-91; and Gao et al 2002, Proc Natl Acad Sci USA, 99(18):11854-9). Briefly, 293 cells were co-transfected with pAdDeltaF6, p5E18-VD2/8 and target vector by calcium phosphate and the virus was harvested by freeze-thawing of the cells, 48h after transfection. The virus was purified by ion exchange column chromatography and iodixanol gradient centrifugation followed by filtration and further concentration against phosphate-buffered saline (PBS)-5% sucrose. Virus titres in terms of genome copies/ml were determined by Q-PCR performed in triplicate, TaqMan (AppliedBiosystems) analysis using primers pr300fw 5' CCCTGTTTGCTCCTCCGATAA3' pr301rv 5' GTCCG-TATTTAAGCAGTGGATCCA 3' amplifying a 95 bp fragment of the hAAT promoter region. Protein composition and purity was determined by sodium dodecyl sulfate-polyacrylamide gel electrophoresis (SDS-PAGE).

1.1.3 Experiment Set-Up

Preliminary Test

In order to test the infective capability and to evaluate the PBGD expression of the AAV2/8 vector, two AIP animals were injected with a dose of $9 \times 10^{12}$ vg of AAV2/8-PBGD and sacrificed at day 6.

Proof-of-Principle Assay

We evaluated the AAV2/8-mediated liver transduction by comparing levels of PBGD expression in the livers of AIP mice after injection of AAV2/8-hBGD. Compound heterozygous AIP mice in C57B1/6 background of 12 to 25 weeks age (10 mice per group 5 males and 5 females) were injected intravenously, via the tail vein, with a total of 100-200 μl corresponding to 5e12 vg/kg of AAV2/8-hPBGD or AAV2/8-luciferase control vector. Two additional groups of five AIP male mice (of the same age that the previous ones) were injected with 5e11 vg/kg or 5e10 vg/kg of AAV2/8-hPBGD. Extra group of wild type and AIP mice will be included. Dose scheme is shown in Table 2.

TABLE 2

Vector doses (Gcs) used as determined by Q-PCR

| AAV2/8 vector | Gs/ml | Gcs/mice | sex | n |
|---|---|---|---|---|
| PBGD | 1.73E12 | 1E11 | ♂ | 5 |
| | | | ♀ | 5 |
| | | 1E10 | ♂ | 5 |
| | | 1E9 | ♂ | 5 |
| Luciferase | 1.79E12 | 1E11 | ♂ | 3 |
| | | | ♀ | 3 |

At fifteen, twenty-eight and ninety days after rAAV vector injection, motor disturbance and porphyrin precursor accumulation was measured in mice before and after the acute attack induced by phenobarbital injection. For this, phenobarbital (Pb, diluted in saline) was administered intraperitoneally once a day on 4 consecutive days with increasing doses (75, 80, 85, 90 mg/kg body weight).

Nerve Conduction Measurement

Electrophysiological studies were carried out to demonstrate axonal degeneration and loss of myelin in sciatic nerve. Two male AIP mice of 6 months old were injected with 1e12 gc/kg. Animals were treated biweekly with repeated doses of Pb to accelerate the motor neuropathy. Nerve conduction measurements were performed in animals at 11 and 14 months old, before and after the acute attack induced by Pb.

1.2. Results 1.2.1 Proof-of-Principle Assay

Effects of Treatment on Heme Precursors Levels Throughout the Study

Fifteen, twenty-eight and ninety days after virus injection, AIP mice were treated with increasing dose of Pb for 4 days and the levels of heme precursors were measured in urine.

As expected, male AIP mice from the control group (AAV-Luc, FIG. 1) displayed increased excretion of precursors after Pb injection, whereas no variation in the excretion of precursors occurred in mice injected with high doses of AAV2/8-PBGD (FIG. 1). Complete avoidance of ALA and PBG accumulation after phenobarbital-induction began at 5e11 vg/kg in male AIP mice (FIG. 1). Partial prevention was observed in AIP males treated with 5e10 vg AAV-PBGD/kg. There were no changes in the profile of phenobarbital-induced ALA and PBG excretion two weeks after the AAV administration and at the end of the study (FIG. 1).

Figure 2:
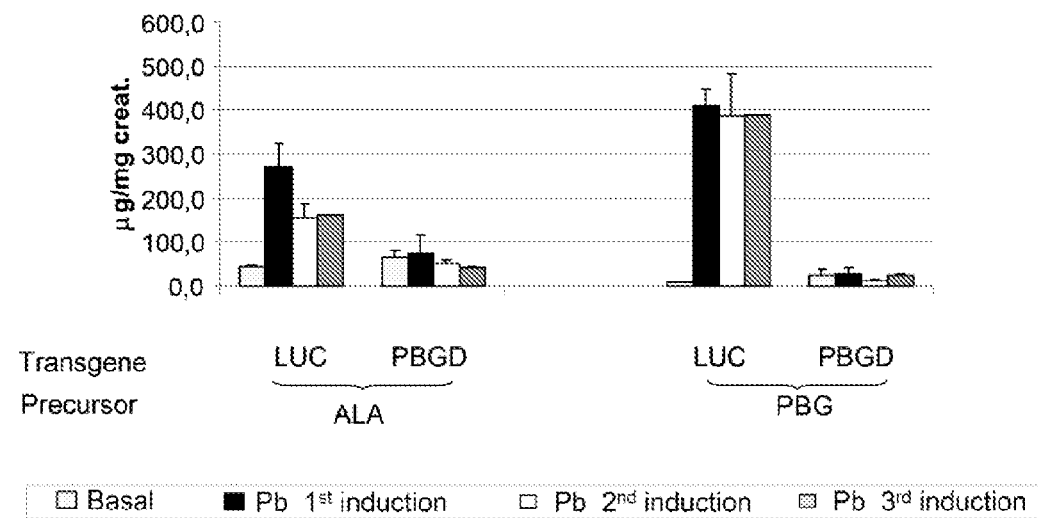
FIG. 2. Urinary excretion of PBG and ALA in female AIP mice after phenobarbital-induced acute attacks after the administration of $5 \times 10^{12}$ vg/kg of therapeutic vector ssAAV2/8-hPBGD or control vector ssAAV2/8-Luc. LUC is luciferase reporter construct; PBGD is various dosages of rAAV-PBGD constructs; Pb is phenobarbital.

The administration of therapeutic vector (5e12 vg of AAV2/8-PBGD/kg) in female animals also prevented Pb-induced acute attacks, as shown by the lack of abnormal accumulation of porphyrin precursors in urine (FIG. 2). In the control group (injected with AAV-Luc), female AIP mice (FIG. 2) exhibited less porphyrin precursor accumulation than male AIP animals (FIG. 1) due to a lower hepatic activity of the rate-limiting ALAS1 enzyme in females when compared to male AIP mice (data not shown).

Figure 13A:
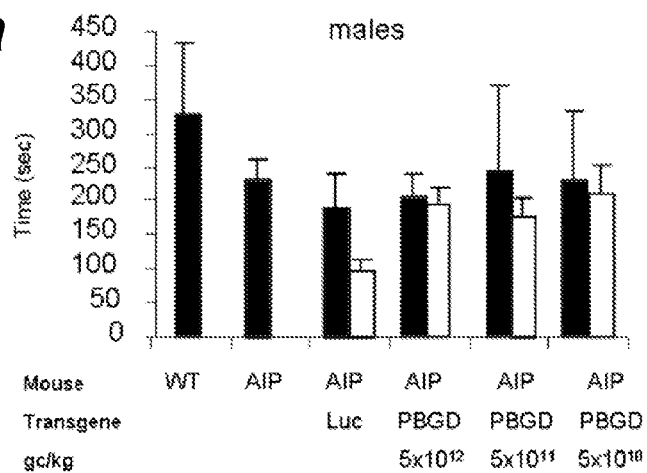
FIG. 13. Rotarod analysis of AIP mouse motor coordination and muscular performance. The length in time that male and female AIP mice could stay on a rotating dowel was measured at the start of the study and upon induction of a porphyria attack 90 days after administration of AAV2/8-PBGD. The porphyric attack was induced by intraperitoneal injection of increasing doses of phenobarbital every 24 hours for four days.
Figure 13B:
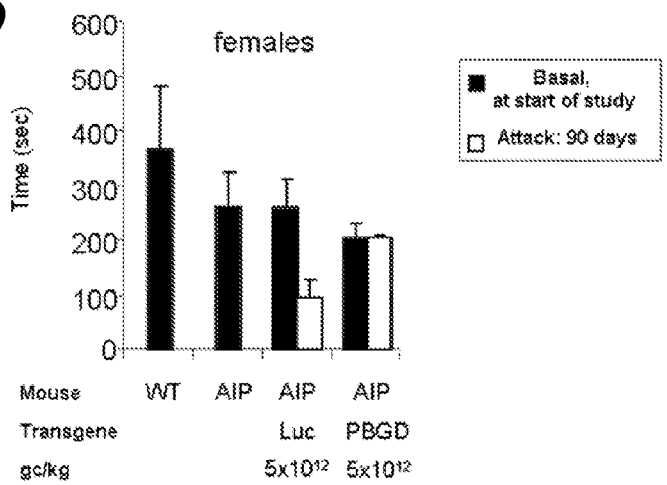

Effects of AAV Administration on Motor Disturbance Throughout the Study: Rotorod Test As expected, AIP mice exhibit motor disturbance when compared with wild type animals. Motor disturbance in AIP mice treated with control vector (AAV-Luc) was exacerbated after phenobarbital administration both in male and female (data not shown). The Pb-induced motor disturbance in male AIP mice was almost completely abolished in animals treated with the therapeutic vector both at the beginning (fifteen and twenty-eight days after the AAV injection, data not shown) and at the end of the study. Male and female AIP animals treated ssAAV2/8-hPBGD showed complete protection against the Pb-induced motor disturbance during the whole period of the study (fifteen and twenty-eight days after the AAV injection, and at the end of the study (FIG. 13). In males, the mean length in time that a mouse that received the luciferase vector could stay on the dowel was approximately 200 seconds. However, upon porphyric attack, this was halved to ~100 seconds. In the males that received all three different doses of PBGD vector, mice could stay on the dowel for nearly as long as when not experiencing an attack, although not to unchallenged wild type levels. The same was also found in females.

Effects of the ssAAV-hPBGD Administration on Liver PBGD Level at Sacrifice: Western Blot Analysis.

Figure 3:
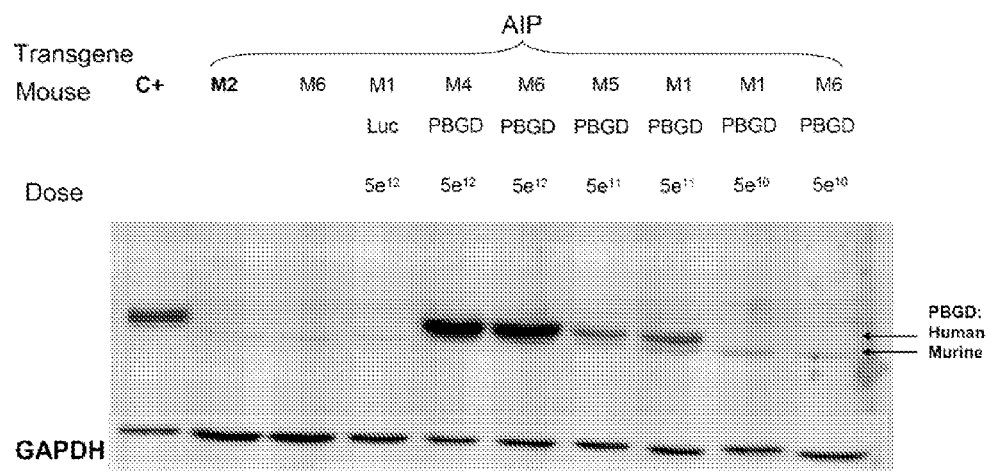
FIG. 3. PBGD transgene expression in the liver of male AIP mice as measured by Western blot analysis.
Figure 4:
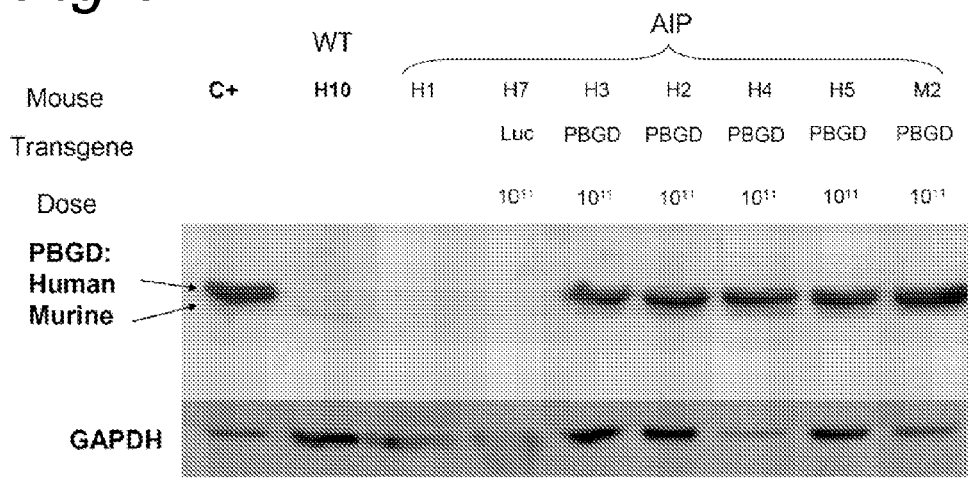
FIG. 4. PBGD transgene expression in the liver of female AIP mice as measured by Western blot analysis.

As expected, the administration of the control vector (ssAAV-Luc) did not increased PBGD expression both in males (FIG. 3) and female mice (FIG. 4). In males, dose-dependant increase of hepatic PBGD expression was observed by western blot analysis (FIG. 3). Different patterns of migration between endogenous and human PBGD allows for identification of exogenous PBGD (FIG. 3).

In females, high expression of PBGD was observed in the liver of mice treated with 5e12 vg/kg of ssAAV-hPBGD (FIG. 4).

Effects of the AAV-PBGD Administration on Liver PBGD Activity at Sacrifice

Figure 5:
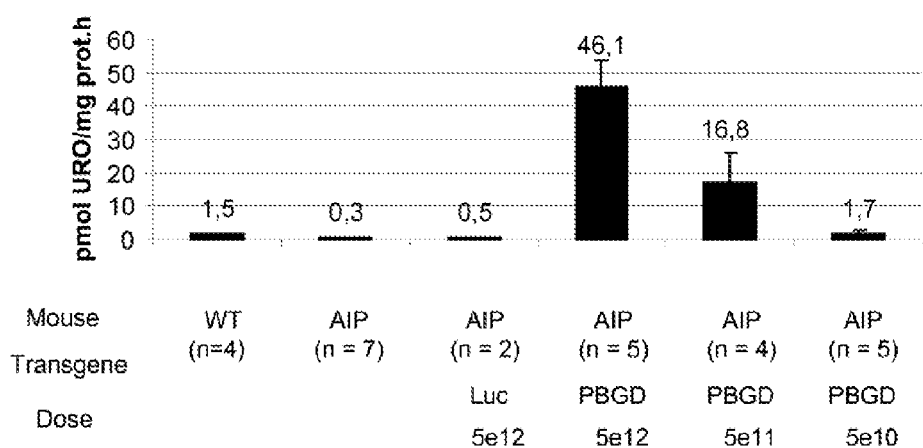
FIG. 5. Hepatic PBGD activity in AIP male mice transduced with ssAAV2/8 at different doses, 3 months post-injection.
Figure 6:
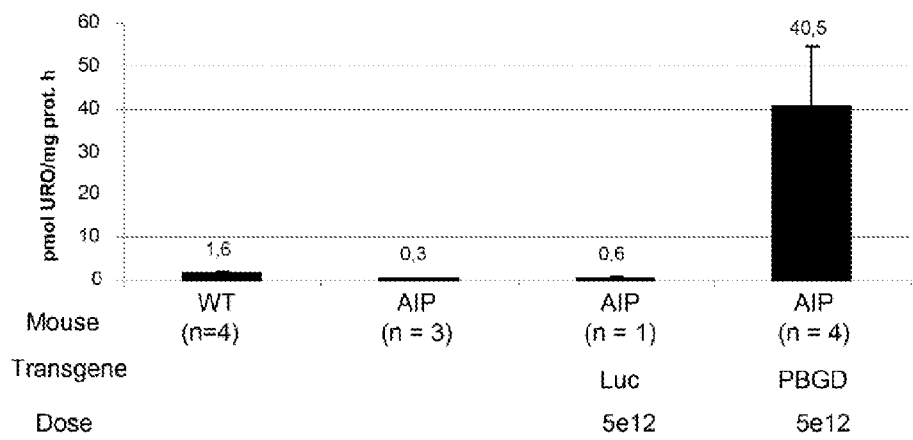
FIG. 6. PBGD activity in the liver of AIP female mice transduced with ssAAV2/8 vector carrying the luciferase or the PBGD gene, 3 months post-injection.

The measurement of enzymatic activity confirms that the PBGD protein expressed by the therapeutic vector is functionally active (FIGS. 5 and 6). No significant differences in the PBGD activity (p=0.35) was observed between males (FIG. 5) and females (FIG. 6) injected with higher doses of the therapeutic vector (AAV-PBGD). In males, a dose-dependant increase of liver PBGD activity was observed (FIG. 5). Mice administered with low doses of therapeutic vector (5e10 vg AAV-PBGD/kg) show the same PBGD activity as wild type animals Immunohistochemistry Analysis: Distribution of the PBGD Expression in the Liver Immunohistochemistry was used to determine PBGD protein levels in individual cells and was performed on duplicate slides for each treatment group. For PBGD immunohistochemical staining a polyclonal antibody anti-PBGD was developed in CIMA. The antibody antiPBGD recognizes the endogenous protein and the exogenous human protein mediated by the ssAAV2/8-hPBGD (data not shown).

The liver of AIP animals injected with the control virus show low expression of PBGD in the cytoplasm of whole hepatocytes as detected by immunohistochemistry analysis (data not shown). This weak signal in the cytoplasm corresponds to the endogenous PBGD. Cell nuclei were counterstained by hematoxylin to give a blue background contrast to brown colour of the positive reaction (data not shown).

In male AIP mice injected with therapeutic vector, a dose-dependant increase of PBGD expression was observed. High PBGD expression was observed in male mice injected with the highest doses of therapeutic virus. The area of strong PBGD expression was reduced in the animals injected with intermediate dose of therapeutic virus and it was reduced to isolated cells in the animals injected with low doses of virus. These results correlate well with those obtained previously by western and enzymatic activity in the same animals.

No significant differences in the PBGD immunohistochemical staining was observed between males and females injected with the same dose of the therapeutic vector (5e12 vg AAV-PBGD/kg). Males and females receiving higher doses of therapeutic vector exhibited a high expression of PBGD in both parenchyma and around the vessels (data not shown).

PBGD was reported to be localized in the cytoplasm of the cells, however it has previously reported that PBGD is imported into the nucleus of various cell lines and of primary cells (Grünberg-Etkovitz et al. 2006, Biochim Biophys Acta. 1762(9): 819-27). In our mice injected with the control virus, most of the nucleus exhibit a characteristic blue stain (due to hematoxylin) and had few nuclei were immunostained brown (due to DAB; data not shown). However, in our mice injected with AAV-PBGD we observed a high proportion of brown, reflecting a high nuclear distribution of PBGD protein. The proportion of high PBGD positive nuclei was measured in different groups. Again, a dose-dependent increase of hepatocytes expressing high nuclear PBGD protein was observed in males.

Neurological Evaluation of Peripheral Neuropathy

Figure 12:
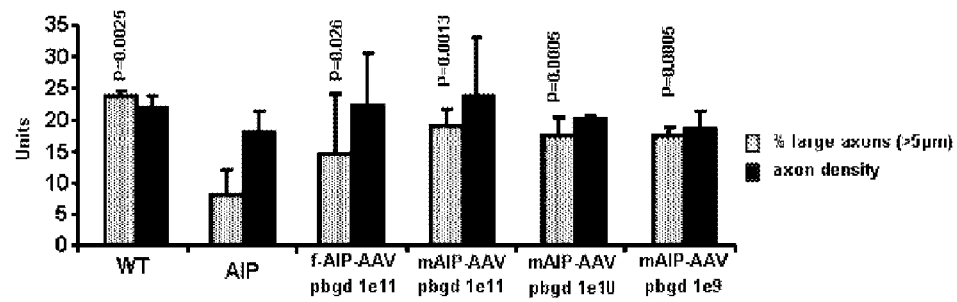
FIG. 12. Neurological evaluation of peripheral neuropathy in AIP mice. The percentage of large axons (5 μm in diameter) and axon density was performed in AIP mice of both genders that received three different doses of rAAV2/8-PBGD. Untreated and wild type (WT) act as controls.

In another aspect, we have performed a neurological evaluation of peripheral neuropathy in AIP mice that included histological analysis of sciatic nerves (data not shown) and functional studies of motor potential evoked by proximal stimulation of the sciatic nerve (data not shown). Normal axon density observed in AIP animals transduced with rAAV2/8-PBGD vector suggested that hPBGD over-expression in the liver facilitated axon regeneration of the sciatic nerve in AIP mice (FIG. 12).

Electrophysiological studies were carried out to demonstrate axonal degeneration and loss of myelin in sciatic nerve. This shows that long term expression of the PBGD transgene protects against functional block induced by phenobarbital administration. Motor potential evoked by proximal stimulation of the sciatic nerve in wild-type, young AIP, old AIP and AIP mice transduced with rAAV2/8-PBGD before and after seven acute attacks of porphyria induced by phenobarbital shows restoration of function in terms of latency, duration and amplitude (data not shown).

Example 2

Increased In Vivo Enzymatic Activity from Codon-optimized PBGD cDNA 2.1 Construction of the Plasmids Used for Hydrodynamic Injection and AAV Gene Delivery with wtPBGD and coPBGD Plasmids used in this study contain expression cassettes with the following elements in a 5' to 3' order: a liver-specific promoter EalbAATp with regulatory sequences from the albumin enhancer (Kramer et al., 2003, Mol Ther. 7(3):375-85), the housekeeping (i.e. non-Erythroid) PBGD cDNA (GenBank acc #X04808). The 3' UTR from the PBGD (bases 1463-1487 GenBank acc #NM_000190) and the PBGD polyadenylation sequence [poly(A) PBGD] (bases 9586-9629 GenBank acc #M95623). The two plasmids containing these expression cassettes are named psl1180-pAAT-PBGD-PolyA PBGD and psl1180-pAAT-coPBGD-PolyA PBGD and differ only in the PBGD coding sequence as explained below.

To generate a codon-optimized PBGD, the gene Bank sequence #NM_000190 corresponding to the human PBGD non-erythroid cDNA was adapted in codon usage to the bias of Homo sapiens (Codon Adaptation Index value 0.97). Further modifications in the coPBGD coding sequence included: 1) A Kozak sequence was introduced to increase translational initiation; 2) Two stop codons were added to ensure efficient termination; and 3) CG content was increased from 55% to 65%. The final coPBGD cDNA, after optimization, has 195 bp changes and 82.1% homology with the original cDNA sequence #NM_000190. This sequence (SEQ ID NO: 1) was synthesized and subcloned in plasmid psl1180-pAAT-PBGD-PolyA PBGD replacing the sequence of the WT PBGD cDNA. The new generated plasmid was named psl1180-pAAT-coPBGD-PolyA PBGD.

The entire expression cassette sequence from plasmids psl1180-pAAT-PBGD-PolyA PBGD and psl1180-pAAT-coPBGD-PolyA PBGD were subcloned in plasmid pVD155, a plasmid containing the 2 ITRs from AAV2. The resulting plasmids named pVD 153 and pVD191 where cotransfected each of them with a parental baculovirus genome into SF9 cells to generate the recombinant baculovirus Bac.VD153 and Bac.VD191. These baculoviruses were used to generate AAV5 vectors in insect cells. Briefly, SF9+ cells were co-infected with 3 different recombinant baculoviruses: Bac.VD92, Bac.VD88 and Bac.VD153 (baculovirus containing the therapeutic EalbAAT-PBGD-polyA). For the production of an AAV5 vector containing the expression cassette EalbAAT-coPBGD-polyA the baculovirus Bac.VD191 was used instead of Bac.VD153.

The AAV5 vector was harvested by freeze-thawing of the cells, 72 h after infection. The vector was purified by affinity column chromatography followed by filtration and further concentration. Virus titres in terms of genome copies/ml were determined by TaqMan Q-PCR, (AppliedBiosystems) analysis using primer hAAT taq reverse 5'CAGCGTCCTGTGTC-CAAGGT3', primer hAAT taq forward 5'AGGCCAACT-TGTCTACGTTTAGTATG3' (both from MWG-Biotech AG) and probe hAAT 5'CTGTAGATCTGTACCCGCCAC-CCCC3' (MWG-Biotech AG). Protein composition and purity was determined by SDS-PAGE.

2.2 Enzymatic PBGD Assays

PBGD activity in tissue homogenates was determined by measuring the conversion of PBG to uroporphyrin according to the method of Anderson and Desnick (Anderson P M, Desnick R J., 1982, Enzyme, 28(2-3):146-57). Briefly, 1 g of tissue was homogenized at 4° C. in 4 volumes of a 1.15% KCl solution. Homogenate was centrifuged at 12.000 rpm at 4° C. for 20 minutes and the clear supernatant without any cellular debris was used the same day for protein determination (Bradford using an albumin standard) and PBGD activity.

The supernatant samples were diluted 1:3 with phosphate buffer (pH 7.6), DTT, $Cl_2Mg$ and Triton X-100; and 100 µl of this mixture was preincubated with 1.8 ml of Tris-HCl 0.1M (pH 8.1) for 3 min at 37° C. Next, the mixture was incubated in the dark with 0.5 ml 1 mM PBG substrate for 60 minutes at 37° C. The reaction was stopped with 350 µl cold TCA 40% and the uroporphyrinogen formed was oxidised to uroporphyrin after light exposure. Uroporphyrins were measured quantitatively using a spectrofluorometer with an excitation peak (λ ext) at 405 nm and window emission peak (λ em) values between 550-660 nm. The PBGD activity was expressed in terms of pmol uroporphyrin/mg protein/hour using appropriate standards.

2.3 Hydrodynamic Injection of PBGD and coPBGD Plasmids

Figure 7:
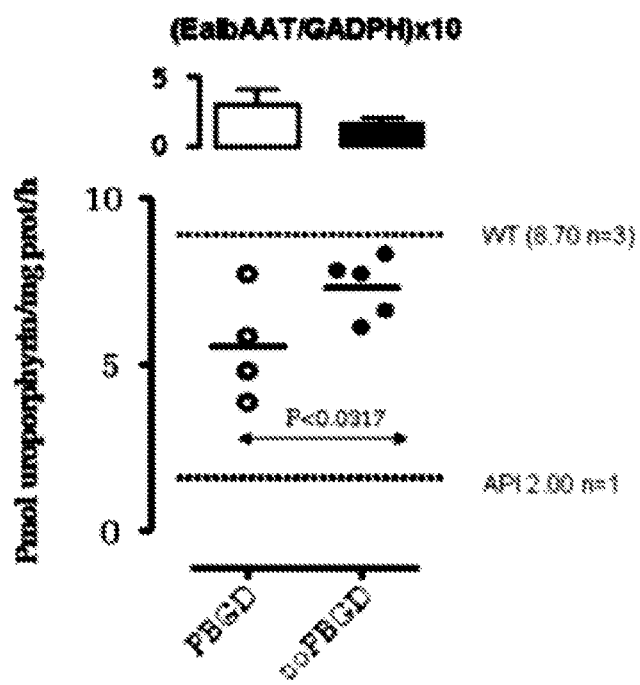
FIG. 7. Comparison of in vivo enzymatic activity of PBGD in wild type (WT mice) and AIP mice (AIP mice) upon hydrodynamic injection of plasmid DNA constructs comprising the wild type PBGD coding sequence (PBGD) and the synthetic, i.e. codon-optimised, PBGD coding sequence of SEQ ID NO: 1 (coPBGD). The levels of vector DNA present in the liver was confirmed by using primers that hybridise to the transgene. Q-PCR-based ratios between the DNA copies of the endogenous housekeeping gene GADPH and the PBGD transgene are indicated above the PBGD enzymatic activities and do not show a significant difference.

50 µg of each plasmid psl1180-pAAT-PBGD-PolyA PBGD or psl1180-pAAT-coPBGD-PolyA PBGD dissolved in 2.5 ml PBS were injected hydrodynamically in the lateral tail vein of AIP mice (n=4) to deliver the plasmid to the liver. Mice were sacrificed 1 week after the injection and PBGD enzymatic activity in the liver and kidney homogenates was determined.

coPBGD enzyme expressed by hepatocytes after hydrodynamic delivery of the psl1180-pAAT-coPBGD-PolyA PBGD plasmid resulted in 30% more active PBGD in liver homogenates compared to mice that received the wild type (wtPBGD) psl1180-pAAT-PBGD-PolyA PBGD plasmid. The values of the PBGD activity expressed as pmol uroporphyrin/mg protein/hour were 5.54±1.64 and 7.30±0.913 for wtPBGD and coPBGD respectively (p=0.0317, two-tailed Mann Whitney test). The levels of vector DNA present in the liver was confirmed by Q-PCR using primers that hybridize to the transgene. A ratio between the DNA copies of the endogenous housekeeping gene GADPH and the DNA copies of the PBGD transgene in each mouse was calculated. DNA ratios (2.950±2.25 and 1.760±0.6804 for PBGD and coPBGD respectively) did not show any significant difference and demonstrated that approximately the same number of copies of the therapeutic vector had been delivered to the liver by hydrodynamic injection. Data are represented in FIG. 7.

2.4 Proof-of-Principle for PBGD Gene Therapy with a PBGD-AAV2/5 Vector in AIP Mice AIP mice described before in section 1.1.1. were used to prove the therapeutic effect of AAV2/5-EalbAAT-PBGD-polyA.

A dose of 5e12 gc/kg of AAV2/5-EalbAAT-PBGD was intravenously injected in AIP mice (males and females). Control animals received the same vector but carrying the luciferase reporter gene. Two, four and thirteen weeks after the AAV2/5-EalbAAT-PBGD administration, animals were treated with increasing doses of Pb for 4 days to induce the porphyric attack. Twenty four hours after the last dose of Pb, the levels of heme precursors were measured in 24 hours-urine samples and motor co-ordination was analysed using the rotarod test. Mice were sacrificed three months after the AAV administration to quantify the amount of PBGD produced in the liver.

Figure 8:
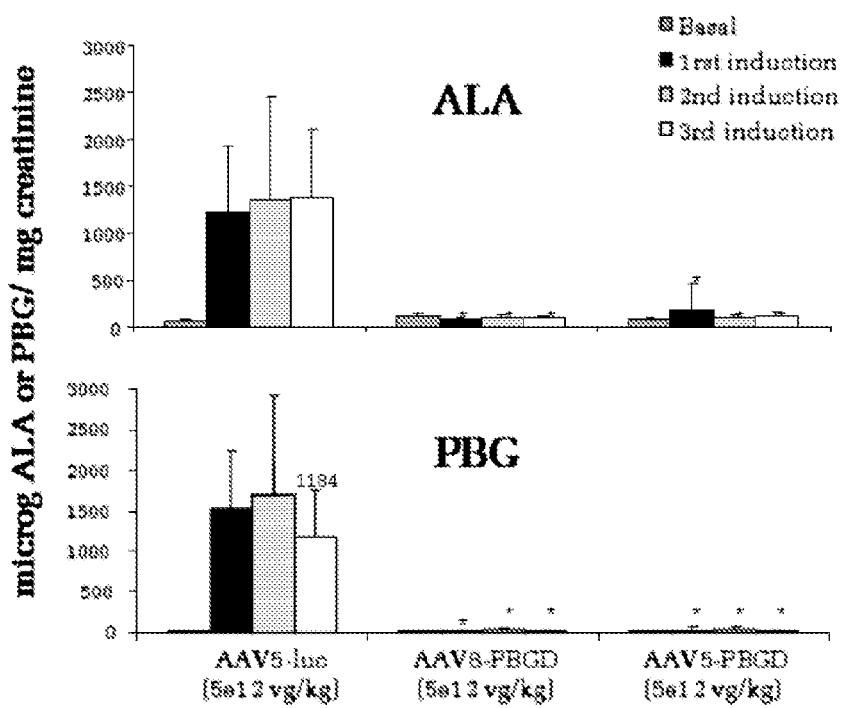
FIGS. 8 and 9. AAV2/5-PBGD protect male (FIG. 8) and female (FIG. 9) mice against phenobarbital-induced acute porphyric attacks. Basal levels of ALA and PBG in AIP mice as well as ALA and PBG level after first, second and third phenobarbital-induced acute porphyric attacks are shown in mice treated with a dose of 5e12 gc/kg control vector (AAV2/5-EalbAAT-Luciferase) and mice treated with 5e12 gc/kg AAV8- and AAV5-PBGD vectors.
Figure 9:
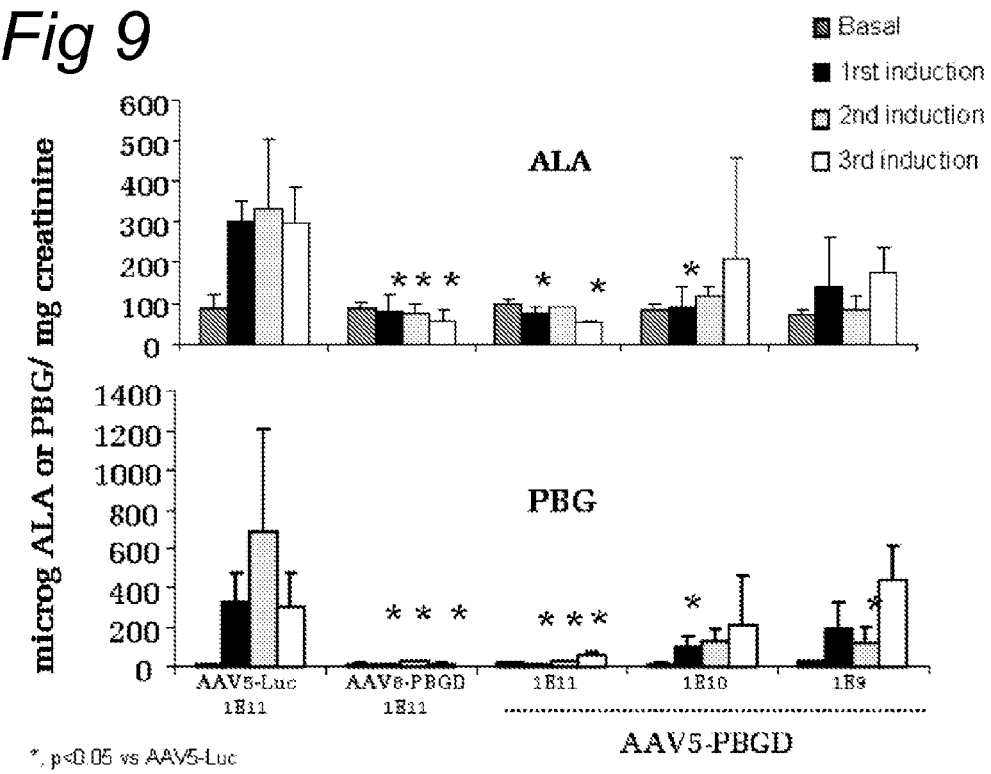

The basal levels of ALA and PBG in AIP mice were: 88±24 and 16±5 µg/mg creatinine in males and 87±19 and 14±8 µg/mg creatinine in females. A dose of 5e12 gc/kg was able to prevent the effect of Pb in the precursors ALA and PBG in both males (118±34 and 11±4 µg/mg creatinine) and females (52±5 and 51±24 µg/mg creatinine) as is shown in FIG. 8 (males) and FIG. 9 (females). Animals treated with the same dose of an AAV2/5-EalbAAT-Luciferase showed a high excretion of ALA and PBG precursors after Pb injection (1418±659 and 1184±585 µg/mg creatinine in males and 295±91 and 298±181 µg/mg creatinine in females).

Motor disturbance induced by Pb treatment in AIP mice was almost completely abolished in animals treated with the therapeutic vector, as measured in the Rotarod test (data not shown).

Figure 10:
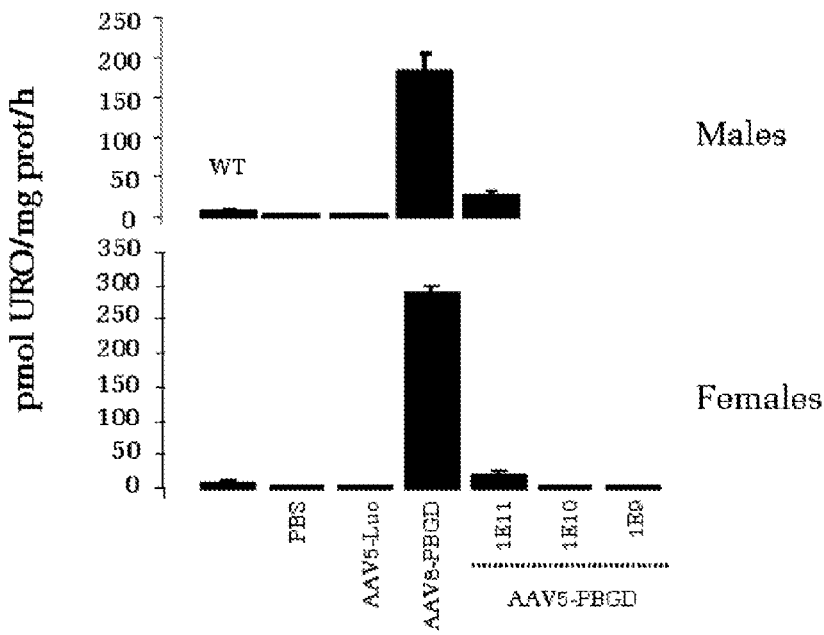
FIG. 10. PBGD enzymatic activity in liver homogenates after AAV8-PBGD and AAV5-LUC administration (n=4-6).

Three months after the AAV administration, all animals were sacrificed and enzymatic PBGD activity measured from livers of all animals (FIG. 10). Males injected with a dose of 5e12 gc/kg of AAV5-EalbAAT-PBGD expressed 26.1±7.3 pmol URO/mg protein/h of PBGD in the liver. This amount represents an over-expression of 10 times when compared with AIP mice receiving reporter gene Luc (2.4 ±0.4 pmol URO/mg protein/h) and 3 times the levels of a wild type mice (7.9±1.6 pmol URO/mg protein/h). A dose of 5e12 gc/kg did reveal differences in the liver PBGD enzymatic activity in females (18.5±6.3 pmol URO/mg protein/h).

2.5 AAV5-Mediated Liver-Specific Expression of PBGD and coPBGD in AIP Mice

Figure 11A:
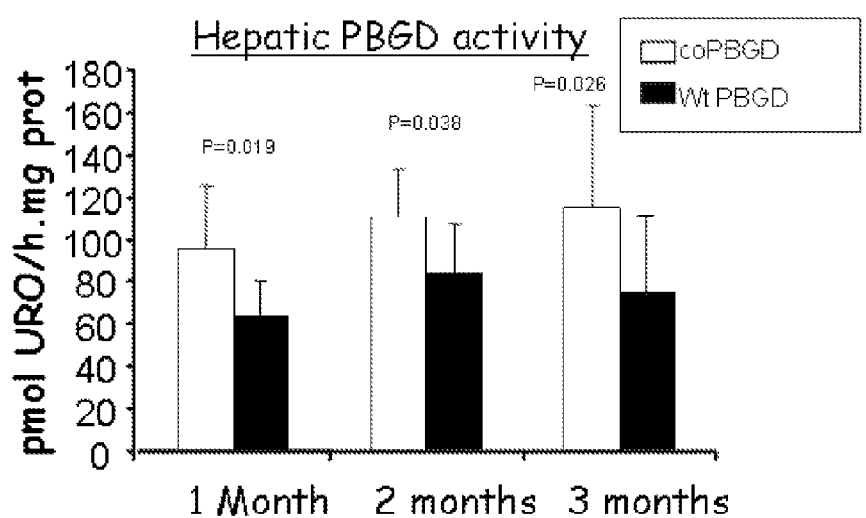
FIG. 11. A. PBGD enzyme activity in liver homogenates of AIP male mice 1, 2 or 3 months after a single injection of $1.25 \times 10^{11}$ gc of ssAAV2/5 vector carrying the PBGD cDNA from human (wt PBGD) or codon optimised PBGD (coPBGD; SEQ ID NO: 1). B. Semi-quantitative PCR analysis of vector copy levels at 1, 2 and 3 months post-injection. C. Representative immunohistochemical analysis of livers from male animals injected with an ssAAV2/5 vector carrying the wtPBGD or coPBGD transgene under the control of the liver specific promoter. D. Proportion of cells stained with PBGD antibody from each cohort of animals.
Figure 11B:
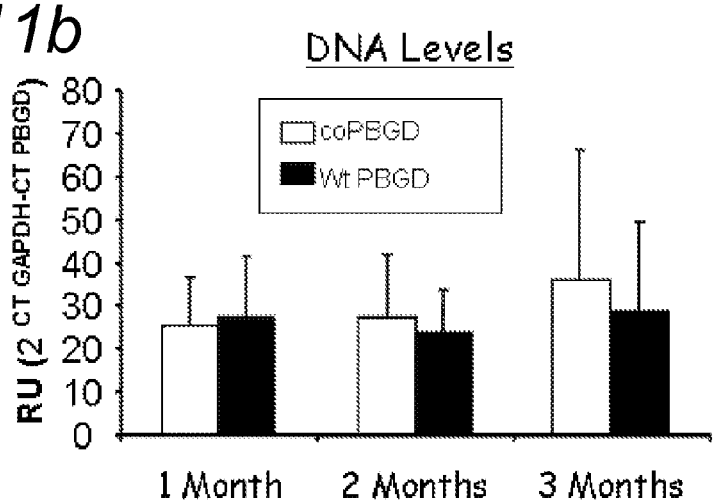
Figure 11C:
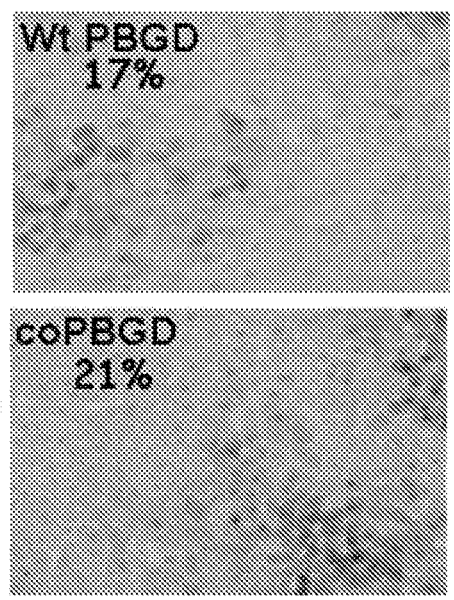
Figure 11D:
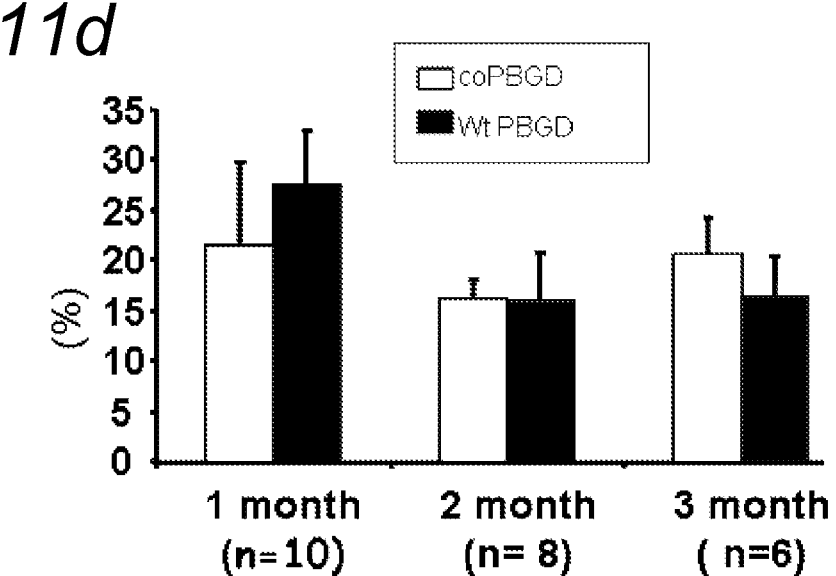

We evaluated the AAV2/5-mediated liver transduction by comparing levels of PBGD expression in the livers of AIP mice after injection of AAV2/5-PBGD or AAV2/5-coPBGD. Male AIP mice in C57B1/6 background of 12 to 25 weeks old were injected intravenously with a total of 200 µl corresponding to 1.25e11 vg of AAV2/5-PBGD (n=22) or AAV2/5-coPBGD (n=24). At 1, 2 and 3 months after virus injection, mice were sacrificed and livers were collected to determine the enzymatic activity of PBGD in liver homogenates. Results were expressed as mean±SEM of the PBGD and comparison between means was performed using the Mann Whitney test (FIG. 11A). In accordance with Lindberg et al., Nature Genetics 12: 195-199, 1996, AIP mice expressed only 30% of the PBGD enzymatic activity in the liver when compared with WT mice (2.53±0.15 vs 7.94±0.94 pmol URO/mg protein/h, respectively). Besides, the levels of PBGD expression after AAV2/5-PBGD and AAV2/5-coPBGD gene transfer were statistically different at all points after administration. 64.00±5.99 vs 86.23±6.82 for AAV2/5-PBGD and AAV2/5-coPBGD respectively after 1 month of infection (p=0.019) and 78.98±9.69 vs 111.50±10.20 AAV2/5-PBGD and AAV2/5-coPBGD respectively after 2 months of infection (p=0.038). Values of enzymatic activity in the murine livers are shown in FIG. 11.A.

Semiquantitative PCR analysis of AAV vector genome was performed. The levels at 1, 2 and 3 months post-injection were determined and are shown in FIG. 11.B. and Q-PCR data corroborate that the amount of viral plasmid was similar in both cohorts of animals The immunohistochemical analysis of the liver with PBGD specific antibodies revealed 17% and 21% of PBGD expressing cells in mice infected with AAV2/5-PBGD and AAV2/5-coPBGD respectively (FIGS. 11.C and D) representing essentially similar transduction efficiencies, which were maintained for the 3 months period of study

The invention claimed is:

1. A method for treating a mammalian subject with acute intermittent porphyria, said method comprising intravenously administering to a mammalian subject in need thereof an effective amount of adeno-associated virus (AAV) virions that comprise:
   (a) a nucleic acid construct comprising the nucleotide sequence as set forth in SEQ ID NO:1 that encodes human porphobilinogen deaminase (PBGD) protein, operably linked to an α1-anti-trypsin (AAT) promoter combined with a mouse albumin gene enhancer (Ealb) element, and AAV serotype 2 inverted terminal repeats (ITRs); and
   (b) capsid proteins from AAV serotypes 1, 2, 5 or 8;
wherein said administration results in expression of the human PBGD protein in the liver of said mammal.

2. The method of claim 1, wherein said AAV virions are administered as a pharmaceutical composition that further comprises a pharmaceutically acceptable carrier.

3. The method of claim 1, wherein the promoter-enhancer element combination consists of the nucleotide sequence as set forth in SEQ ID NO: 5.

4. The method of claim 2, wherein the promoter-enhancer element combination consists of the nucleotide sequence as set forth in SEQ ID NO: 5.

5. The method of claim 4, wherein the subject is a human.

* * * * *